United States Patent
Pauls et al.

(10) Patent No.: US 12,329,805 B2
(45) Date of Patent: Jun. 17, 2025

(54) DOSAGE FORMS OF TISSUE KALLIKREIN 1

(71) Applicant: DiaMedica Inc., Kelowna (CA)

(72) Inventors: Rick Pauls, Minnetonka, MN (US); Todd Verdoorn, Minnetonka, MN (US)

(73) Assignee: DiaMedica Inc., Kelowna (CA)

( * ) Notice: Subject to any disclaimer, the term of this patent is extended or adjusted under 35 U.S.C. 154(b) by 0 days.

(21) Appl. No.: 18/501,804

(22) Filed: Nov. 3, 2023

(65) Prior Publication Data

US 2024/0238389 A1    Jul. 18, 2024

Related U.S. Application Data

(62) Division of application No. 16/492,059, filed as application No. PCT/US2018/021749 on Mar. 9, 2018, now Pat. No. 11,857,608.

(60) Provisional application No. 62/567,406, filed on Oct. 3, 2017, provisional application No. 62/516,463, filed on Jun. 7, 2017, provisional application No. 62/469,385, filed on Mar. 9, 2017.

(51) Int. Cl.
*A61K 38/48* (2006.01)
*A61K 9/00* (2006.01)
*A61K 45/06* (2006.01)

(52) U.S. Cl.
CPC ........ *A61K 38/4853* (2013.01); *A61K 9/0019* (2013.01); *A61K 45/06* (2013.01); *C12Y 304/21035* (2013.01)

(58) Field of Classification Search
None
See application file for complete search history.

(56) References Cited

U.S. PATENT DOCUMENTS

| | | |
|---|---|---|
| 3,472,931 A | 10/1969 | Stoughton et al. |
| 3,527,864 A | 9/1970 | MacMillan et al. |
| 3,896,238 A | 7/1975 | Smith |
| 3,903,256 A | 9/1975 | MacMillan et al. |
| 3,952,099 A | 4/1976 | Smith |
| 4,046,886 A | 9/1977 | Smith |
| 4,130,643 A | 12/1978 | Smith |
| 4,130,667 A | 12/1978 | Smith |
| 4,146,613 A | 3/1979 | Dietze et al. |

(Continued)

FOREIGN PATENT DOCUMENTS

| | | |
|---|---|---|
| CA | 2415392 A1 | 1/2002 |
| CA | 2465632 A1 | 5/2003 |

(Continued)

OTHER PUBLICATIONS

Abdelaziz, A. et al., "Glucose homeostasis in the nonobese diabetic mouse at the prediabetic stage," Endocrinology, 139:1115-1124 (1998).

(Continued)

*Primary Examiner* — Erin M. Bowers
(74) *Attorney, Agent, or Firm* — COOLEY LLP

(57) ABSTRACT

Provided are dosage forms of one or more tissue kallikrein-1 (KLK1) polypeptides which have a total KLK1 polypeptide dosage of about 0.1 µg/kg to about 10.0 µg/kg, including subcutaneous and intravenous dosage forms. Also provided are related devices and methods of use thereof, for example, for treating ischemic and hemorrhagic conditions.

18 Claims, 5 Drawing Sheets

Specification includes a Sequence Listing.

| Cohort | Patients N | Day -1 FBG¹ (mmol/L) | ΔFBG Mean | 95% CI |
|---|---|---|---|---|
| Placebo | 12 | 9.48 (1.2) | -0.927 | (-2.019, 0.164) |
| Low 3 µg/kg | 13 | 10.425 (2.1) | -0.925 | (-1.743, -0.107) |
| High 15 µg/kg | 12 | 10.458 (1.5) | -0.025 | (-0.651, 0.601) |

¹Mean (SD)                                                    *P<0.05

(56) References Cited

U.S. PATENT DOCUMENTS

| | | |
|---|---|---|
| 4,150,121 A | 4/1979 | Dietze et al. |
| 4,299,826 A | 11/1981 | Luedders |
| 4,315,988 A | 2/1982 | Miwa et al. |
| 4,335,115 A | 6/1982 | Thompson et al. |
| 4,343,798 A | 8/1982 | Fawzi |
| 4,379,454 A | 4/1983 | Campbell et al. |
| 4,405,616 A | 9/1983 | Rajadhyaksha |
| 4,439,196 A | 3/1984 | Higuchi |
| 4,447,224 A | 5/1984 | DeCant, Jr. et al. |
| 4,447,233 A | 5/1984 | Mayfield |
| 4,474,893 A | 10/1984 | Reading |
| 4,475,196 A | 10/1984 | La Zor |
| 4,486,194 A | 12/1984 | Ferrara |
| 4,487,603 A | 12/1984 | Harris |
| 4,666,828 A | 5/1987 | Gusella |
| 4,676,980 A | 6/1987 | Segal et al. |
| 4,683,202 A | 7/1987 | Mullis |
| 4,689,042 A | 8/1987 | Sarnoff et al. |
| 4,746,515 A | 5/1988 | Cheng et al. |
| 4,788,062 A | 11/1988 | Gale et al. |
| 4,801,531 A | 1/1989 | Frossard |
| 4,816,567 A | 3/1989 | Cabilly et al. |
| 4,820,720 A | 4/1989 | Sanders et al. |
| 4,835,253 A | 5/1989 | Burton |
| 4,863,738 A | 9/1989 | Taskovich |
| 4,863,970 A | 9/1989 | Patel et al. |
| 4,925,678 A | 5/1990 | Ranney |
| 4,959,217 A | 9/1990 | Sanders et al. |
| 5,124,322 A | 6/1992 | Hughes |
| 5,167,616 A | 12/1992 | Haak et al. |
| 5,169,383 A | 12/1992 | Gyory et al. |
| 5,187,305 A | 2/1993 | Thompson et al. |
| 5,192,659 A | 3/1993 | Simons |
| 5,223,409 A | 6/1993 | Ladner et al. |
| 5,225,182 A | 7/1993 | Sharma |
| 5,234,956 A | 8/1993 | Lipton |
| 5,253,785 A | 10/1993 | Haber et al. |
| 5,262,430 A | 11/1993 | Borrevang et al. |
| 5,272,057 A | 12/1993 | Smulson et al. |
| 5,370,862 A | 12/1994 | Klokkers-Bethke et al. |
| 5,378,730 A | 1/1995 | Lee et al. |
| 5,403,484 A | 4/1995 | Ladner et al. |
| 5,403,486 A | 4/1995 | Leung |
| 5,462,739 A | 10/1995 | Dan et al. |
| 5,478,323 A | 12/1995 | Westwood et al. |
| 5,516,639 A | 5/1996 | Tindall et al. |
| 5,534,615 A | 7/1996 | Baker et al. |
| 5,561,165 A | 10/1996 | Lautt et al. |
| 5,571,698 A | 11/1996 | Ladner et al. |
| 5,580,576 A | 12/1996 | Veronesi et al. |
| 5,614,192 A | 3/1997 | Vandenbark |
| 5,648,095 A | 7/1997 | Illum et al. |
| 5,656,722 A | 8/1997 | Dorschug |
| 5,698,738 A | 12/1997 | Garfield et al. |
| 5,716,617 A | 2/1998 | Khandke et al. |
| 5,744,487 A | 4/1998 | Ohshima et al. |
| 5,762,922 A | 6/1998 | Noble et al. |
| 5,789,447 A | 8/1998 | Wink, Jr. et al. |
| 5,874,531 A | 2/1999 | Strominger et al. |
| 5,902,829 A | 5/1999 | Schneider et al. |
| 5,906,987 A | 5/1999 | Chwalisz et al. |
| 5,910,316 A | 6/1999 | Keefer et al. |
| 5,958,427 A | 9/1999 | Salzman et al. |
| 5,980,896 A | 11/1999 | Hellstrom et al. |
| 6,165,975 A | 12/2000 | Adams et al. |
| 6,171,232 B1 | 1/2001 | Papandreou et al. |
| 6,221,633 B1 | 4/2001 | Ertl et al. |
| 6,277,558 B1 | 8/2001 | Hudson |
| 6,288,040 B1 | 9/2001 | Muller et al. |
| 6,303,606 B1 | 10/2001 | Leonardi et al. |
| 6,307,027 B1 | 10/2001 | Linemeyer et al. |
| 6,358,536 B1 | 3/2002 | Thomas |
| 6,369,071 B1 | 4/2002 | Haj-Yehia |
| 6,436,996 B1 | 8/2002 | Vitek et al. |
| 6,492,405 B2 | 12/2002 | Haj-Yehia |
| 6,586,438 B2 | 7/2003 | Piper |
| 6,887,872 B2 | 5/2005 | Literati et al. |
| 6,962,793 B2 | 11/2005 | Diamandis |
| 7,087,247 B2 | 8/2006 | Li et al. |
| 7,195,759 B2 | 3/2007 | Sabbadini et al. |
| 7,622,447 B2 | 11/2009 | Lautt et al. |
| 7,723,326 B2 | 5/2010 | Lagu et al. |
| 8,058,019 B2 | 11/2011 | Roggenbuck |
| 8,501,695 B2 | 8/2013 | Williams |
| 8,673,964 B2 | 3/2014 | Lautt |
| 9,364,521 B2 | 6/2016 | Charles et al. |
| 9,616,015 B2 | 4/2017 | Charles |
| 9,839,678 B2 | 12/2017 | Charles et al. |
| 11,857,608 B2 | 1/2024 | Pauls et al. |
| 2001/0056068 A1 | 12/2001 | Chwalisz et al. |
| 2002/0106368 A1 | 8/2002 | Bot et al. |
| 2002/0192723 A1 | 12/2002 | Yoo |
| 2003/0045553 A1 | 3/2003 | Bussolari et al. |
| 2003/0114469 A1 | 6/2003 | Cohen |
| 2003/0158090 A1 | 8/2003 | Pedersen-Bjergaard et al. |
| 2003/0166662 A1 | 9/2003 | Fryburg et al. |
| 2003/0181461 A1 | 9/2003 | Lautt et al. |
| 2003/0216306 A1 | 11/2003 | Sabbadini et al. |
| 2003/0235609 A1 | 12/2003 | Lautt |
| 2004/0058258 A1 | 3/2004 | Yoshino et al. |
| 2004/0068005 A1 | 4/2004 | Szilvassy et al. |
| 2004/0151785 A1 | 8/2004 | Lautt |
| 2004/0209849 A1 | 10/2004 | Fischer |
| 2004/0253226 A1 | 12/2004 | Holaday et al. |
| 2005/0049293 A1 | 3/2005 | Lautt |
| 2007/0009438 A1 | 1/2007 | Lautt |
| 2007/0224209 A1 | 9/2007 | Berczi et al. |
| 2007/0238762 A1 | 10/2007 | Lautt |
| 2008/0004432 A1 | 1/2008 | Ruben et al. |
| 2009/0162342 A1 | 6/2009 | Berczi et al. |
| 2009/0233995 A1 | 9/2009 | Lautt |
| 2009/0324701 A1 | 12/2009 | Williams |
| 2010/0008899 A1 | 1/2010 | Williams |
| 2010/0226910 A1 | 9/2010 | Williams |
| 2011/0150781 A1 | 6/2011 | Charles et al. |
| 2012/0070425 A1 | 3/2012 | Williams et al. |
| 2012/0201804 A1 | 8/2012 | Williams et al. |
| 2012/0225051 A1 | 9/2012 | Williams et al. |
| 2012/0276019 A1 | 11/2012 | Charles et al. |
| 2013/0089564 A1 | 4/2013 | Berczi et al. |
| 2013/0224230 A1 | 8/2013 | Berczi et al. |
| 2013/0280235 A1 | 10/2013 | Williams |
| 2013/0315891 A1 | 11/2013 | Charles |
| 2013/0323222 A1* | 12/2013 | Charles ............... C12N 9/6445 424/94.3 |
| 2014/0134152 A1 | 5/2014 | Willimas et al. |
| 2015/0196624 A1 | 7/2015 | Charles et al. |
| 2016/0000704 A1 | 1/2016 | Charles |
| 2017/0119862 A1 | 5/2017 | Charles et al. |
| 2021/0138045 A1 | 5/2021 | Pauls et al. |
| 2023/0414727 A1 | 12/2023 | Pauls |

FOREIGN PATENT DOCUMENTS

| | | |
|---|---|---|
| CA | 2659012 A1 | 1/2008 |
| CA | 2756801 A1 | 9/2010 |
| CN | 1384199 A | 12/2002 |
| CN | 101255438 A | 9/2008 |
| CN | 104830822 B | 2/2017 |
| DE | 4420523 A1 | 12/1995 |
| DE | 102008003566 A1 | 7/2009 |
| DE | 102008003568 A1 | 7/2009 |
| EP | 0368187 B1 | 9/1993 |
| EP | 0419504 B1 | 1/1994 |
| EP | 0214826 B1 | 10/1994 |
| EP | 0297913 B1 | 2/1995 |
| EP | 0383472 B1 | 2/1996 |
| EP | 0375437 B1 | 9/1998 |
| EP | 0678522 B1 | 1/2002 |
| EP | 0835139 B1 | 9/2003 |
| EP | 0885961 B1 | 12/2004 |
| GB | 1572146 A | 7/1980 |
| JP | S5386042 A | 7/1978 |
| JP | S57114512 A | 7/1982 |

(56) References Cited

FOREIGN PATENT DOCUMENTS

| | | |
|---|---|---|
| JP | 2009544630 A | 12/2009 |
| KR | 101959952 B1 | 3/2019 |
| KR | 102408525 B1 | 6/2022 |
| KR | 102511477 B1 | 3/2023 |
| WO | WO-8900192 A1 | 1/1989 |
| WO | WO-8910937 A1 | 11/1989 |
| WO | WO-9117767 A1 | 11/1991 |
| WO | WO-9200321 A1 | 1/1992 |
| WO | WO-9218002 A1 | 10/1992 |
| WO | WO-0007575 A2 | 2/2000 |
| WO | WO-0019992 A1 | 4/2000 |
| WO | WO-0053776 A2 | 9/2000 |
| WO | WO-0102039 A1 | 1/2001 |
| WO | WO-0136611 A1 | 5/2001 |
| WO | WO-0156532 A2 | 8/2001 |
| WO | WO-0213798 A2 | 2/2002 |
| WO | WO-03028730 A2 | 4/2003 |
| WO | WO-2004029238 A1 | 4/2004 |
| WO | WO-2004058258 A1 | 7/2004 |
| WO | WO-2005022146 A2 | 3/2005 |
| WO | WO-2005022164 A2 | 3/2005 |
| WO | WO-2005112949 A1 | 12/2005 |
| WO | WO-2006008002 A2 | 1/2006 |
| WO | WO-2006017538 A2 | 2/2006 |
| WO | WO-2008011713 A1 | 1/2008 |
| WO | WO-2008016883 A2 | 2/2008 |
| WO | WO-2008134512 A1 | 11/2008 |
| WO | WO-2009012571 A1 | 1/2009 |
| WO | WO-2009039704 A1 | 4/2009 |
| WO | WO-2010009557 A1 | 1/2010 |
| WO | WO-2010080833 A1 | 7/2010 |
| WO | WO-2010108262 A1 | 9/2010 |
| WO | WO-2010121358 A1 | 10/2010 |
| WO | WO-2010121361 A1 | 10/2010 |
| WO | WO-2012075342 A2 | 6/2012 |
| WO | WO-2012154574 A1 | 11/2012 |
| WO | WO-2013173923 A1 | 11/2013 |
| WO | WO-2013181755 A1 | 12/2013 |
| WO | WO-2014059536 A1 | 4/2014 |
| WO | WO-2015195842 A1 | 12/2015 |
| WO | WO-2017120537 A1 | 7/2017 |
| WO | WO-2018165551 A1 | 9/2018 |
| WO | WO-2023196860 A1 | 10/2023 |

OTHER PUBLICATIONS

Abdelhaleem et al., "Identification of immunosuppressive fractions from the rat submandibular salivary gland," Immunology (1992) 76:331-337.
Adams, D. H. et al., "Transforming growth factor-β induces human T lymphocyte migration in vitro," The Journal of Immunology, Jul. 15, 1991;147(2):609-612.
Albertini, R. et al., "Kallikrein-kinin system in one- and two-kidney Goldblatt hypertensive rats," Clinical Science (Lond)., Mar. 1979, 56(3):227-233.
Alhenc-Gelas et al., "Measurement of urinary kallikrein activity: Species differences in kinin production," Biochimica et Biophysica Acta (1981) 677:477-488.
Allen et al., "Rapid onset synovial inflammation and hyperplasia induced by transforming growth factor β," The Journal of Experimental Medicine, (1990) 171:231-247.
Angermann et al., "Purification and characterization of human salivary-gland prokallikrein from recombinant baculovirus-infected insect cells," Eur. J. Biochem. (1992) 206:225-233.
Assan et al., "Metabolic and Immunological Effects of Cyclosporin in Recently Diagnosed Type 1 Diabetes Mellitus," The Lancet, p. 67-71, Jan. 12, 1995.
Atkinson et al., "Islet Cell Autoantigens in Insulin-Dependent Diabetes," Adkinson and Maclaren, Islet Cell Autoangtigens in Diabetes, J Clin Invest 92, pp. 1608-1616, 1993.
Atkinson, M. A. et al., "Type 1 diabetes: New perspectives on disease pathogenesis and treatment," Lancet 2001; 358:221-229.

Auger, I. et al., "New autoantigens in rheumatoid arthritis (RA): screening 8268 protein arrays with sera from patients with RA," Annals of the Rheumatic Diseases, 68:591-594 (2009).
Baggio, Laurie L., et al., "A recombinant human glucagon-like peptide (GLP)-1-albumin protein (albugon) mimics peptidergic activation of GLP-1 receptor-dependent pathways coupled with satiety, gastrointestinal motility, and glucose homeostasis", Diabetes (2004); 53(9): 2492-2500.
Barnett et al., "Treatment of rheumatoid arthritis with oral Type II Collagen," Arthritis & Rheumatism (1998) 41(2):290-297.
Baumgarten et al., "Concentrations of glandular kallikrein in human nasal secretions increase during experimentally induced allergic rhinitis," The Journal of Immunology (1986) 137(4):1323-1328.
Benson et al., "Oral administration of myelin basic protein is superior to myelin in suppressing established relapsing experimental autoimmune encephalomyelitis," The Journal of immunology, 162:6247-6254 (1999).
Berczi et al., "The influence of pituitary hormones on adjuvant arthritis," Arthritis and Rheumatism (1984) 27(6):682-688.
Bhoola et al., "Bioregulation of kinins: Kallikreins, kininogens, and kininases," Pharmacological Reviews, 44(1):1-80 (1992).
Bindseil et al., "Pure compound libraries; a new perspective for natural product based drug discovery," Drug Discovery Today, 6(16):840-847 (2001).
Blanchard, et al., Partial human genetic deficiency in tissue kallikrein activity and renal calcium handling, Clinical Journal of the American Society of Nephrology, Mar. 2007, pp. 320-325.
Blaukat, A. et al., "Regulation of Cardiovascular Signaling by Kinins and Products of Similar Converting Enzyme Systems— Downregulation of bradykinin B2 receptor in human fibroblasts during prolonged agonist exposure," American Journal of Physiology, Heart and Circulatory Physiology, 284(6):1H909-H1916 (2003).
Bodin et al., "Kallikrein protects against micro albuminuria in experimental type I diabetes," Kidney International, 76(4):395-403 (2009).
Bolan et al., "In vivo micro-MRI of intracortical neurovasculature," Neuroimage, 32:62-69 (2006).
Born et al., "Sniffing neuropeptides: a transnasal approach to the human brain," Nature Neuroscience, 5(6):514-516 (2002).
Bothwell, M. A. et al., "The relationship between glandular kallikrein and growth factor-processing proteases of mouse submaxillary gland," The Journal of Biological Chemistry, Aug. 10, 1979;254(15):7287-7294.
Brandes et al., "Type I transforming growth factor-β receptors on neutrophils mediate chemotaxis to transforming growth factor-β," The Journal of Immunology (1991) 147(5):1600-1606.
Caperuto et al., "Modulation of bone morphogenetic protein-9 expression and processing by insulin, glucose, and glucocorticoids: possible candidate for hepatic insulin-sensitizing substance," Endocrinology, 149(12):6326-6335 (2008).
Carlson, M. W. et al., "Chronic ulcerative stomatitis: evidence of autoimmune pathogenesis," Oral Surgery, Oral Medicine, Oral Pathology, Oral Radiology, and Endodontology, 111:742-748 (2011).
Castiglioni, et al., Detecting sodium-sensitivity in hypertensive patients: information from 24-hour ambulatory blood pressure monitoring, Hypertension, Feb. 2011, pp. 180-185.
Castro et al., "Does the Kunitz domain from the Alzheimer's amyloid β protein precursor inhibit a kallikrein responsible for post-translational processing of nerve growth factor precursor," FEBS Lett., 267(2):207-212 (1990).
Chan, H. et al., "Expression and characterization of human tissue kallikrein variants," Protein Expr. And Purifi., Apr. 1998;12(3):361-370.
Chao, J. et al., "Experimental therapy with tissue kallikrein against cerebral ischemia," Frontiers in Bioscience, 11:1323-1327 (2006).
Chao, J. et al., "Functional analysis of human tissue kallikrein in transgenic mouse models," Hypertension, Mar. 1996;27(3 Pt 2):491-494.
Chatzigeorgiou et al., "The Use of Animal Models in the Study of Diabetes Mellitus," In Vivo, Mar.-Apr. 2009;23(2):245-258.
Chen et al., "Beneficial effects of kallikrein-binding protein in transgenic mice during endotoxic shock," Life Sciences (1997) 60(17):1431-1435.

(56) References Cited

OTHER PUBLICATIONS

Christensen, M. et al., "Lixisenatide, a novel GLP-1 receptor agonist for the treatment of type 2 diabetes mellitus," IDrugs, 12(8):503-513 (2009).
Christiansen et al., "Detection of tissue kallikrein in the bronchoalveolar lavage fluid of asthmatic subjects," J. Clin. Invest. (1987) 79:188-197.
Clements, J. A., "The human kallikrein gene family: a diversity of expression and function," Molecular and Cellular Endocrinology, 99:C1-C6 (1994).
Clements, J. et al., "The expanded human kallikrein (KLK) gene family: Genomic organization, tissue-specific expression and potential functions," Biological Chemistry, 382(1):5-14 (2001).
Coker et al., "Role of hepatic α- and β-adrenergic receptor stimulation on hepatic glucose production during heavy exercise," American Journal of Physiology, Endocrinology and Metabolism, 273:E831-E838 (1997).
Coniglio, et al., Transthyretin V142I genetic variant and cardiac remodeling, injury, and heart failure risk in black adults, Heart Failure, Feb. 2022, pp. 129-138.
Croxatto, H. R. et al., "Inhibition of urinary kallikrein excretion by semi-purified renin in the rat," Clinical Science, 57:243s-245s (1979).
Cull et al., "Screening for receptor ligands using large libraries of peptides linked to C terminus of the lac repressor," PNAS, 89:1865-1869 (1992).
Cwirla, et al. Peptides on phage: a vast library of peptides for identifying ligands, Proceedings of the National Academy of Sciences, Aug. 1990, pp. 6378-6382.
Damas, J. et al., "The kallikrein-kinin system, angiotensin converting enzyme inhibitors and insulin sensitivity," Diabetes/Metabolism Research and Reviews, 20(4):288-297 (2004).
Davis et al., "Calibrated functional MRI: Mapping the dynamics of oxidative metabolism," Proc. Natl. Acad. Sci. USA, 95:1834-1839 (1998).
Dertzbaugh et al., "Comparative effectiveness of cholera toxin B subunit and alkaline phosphatase as carriers for oral vaccines," Infection and Immunity (1993) 61(1):48-55.
Desrivieres, S. et al., "Activation of the 92 kDa type IV collagenase by tissue kallikrein," Journal of Cellular Physiology, 157:587-593 (1993).
Devasahayam, "Factors affecting the expression of recombinant glycoproteins," Indian J Med Research, Jul. 2007;126:22-27.
Devlin et al., "No excess of homozygosity at loci used for DNA fingerprinting," Science, 249 (4975):1416-1420 (1990).
DeWitt, S. Hobbs, et al. ""Diversomers": An approach to nonpeptide, nonoligomeric chemical diversity." Proceedings of the National Academy of Sciences USA (1993); 90.15: 6909-6913.
Diamandis, E. P. et al., "Human kallikrein 6 as a biomarker of Alzheimer's disease," Clinical Biochemistry, 33:663-667 (2000).
Dodge, G. R. et al., "Immunohistochemical detection and immunochemical analysis of type II collagen degradation in human normal, rheumatoid, and osteoarthritic articular cartilages and in explants of bovine articular cartilage cultured with interleukin 1," J. Clin. Invest. 83:647-661 (1989).
Dong, Y. et al., "Tissue-specific promoter utilisation of the kallikrein-related peptidase genes, KLK5 and KLK7, and cellular localisation of the encoded proteins suggest roles in exocrine pancreatic function," Biological Chemistry, 389(2):99-109 (Feb. 2008).
Doyle, B. L. et al., "Biophysical signatures of noncovalent aggregates formed by a glucagonlike peptide-1 analog: a prototypical example of biopharmaceutical aggregation," J. Pharm. Sci., 94(12):2749-2763 (2005).
Dunbar et al., "Central Adrenergic Suppression Augments the Insulin and Glucagon Secretory, and the Glycogenolytic Responses in Streptozotocin-Diabetic Rats," Hormone Research, 36:80-85 (1991).
Ebringer, A et al., "'B27 Disease' Is a New Autoimmune Disease That Affects Millions of People," Annals of the New York Academy of Sciences, 1110:112-120 (2007).

Edgerton et al., "Inhaled Insulin is Associated with Prolonged Enhancement of Glucose Disposal in Muscle and Liver in the Canine," J Pharmacal Exp Ther., Mar. 2009; 328(3):970-975.
Eldefrawi et al., "Purification and molecular properties of the acetylcholine receptor from Torpedo Electroplax," Archives of Biochemistry and Biophysics, (1973) 159:362-373.
Ellingsgaard et al., "Interleukin-6 regulates pancreatic alpha-cell mass expansion," PNAS USA, 105(35): 13163-13168 (Sep. 2008), Published online Aug. 21, 2008.
Emami, N. et al., "Utility of kallikrein-related peptidases (KLKs) as cancer biomarkers, Clinical Chemistry, 54(10):1600-1607 (2008).
Emamian, E. S. et al., "Convergent evidence for impaired AKT1-GSK3β signaling in schizophrenia," Nature Genetics, 36(2):131-137 (2004).
Emanueli, C. et al., "Prophylactic Gene Therapy With Human Tissue Kallikrein Ameliorates Limb Ischemia Recovery in Type 1 Diabetic Mice," Diabetes, 53:1096-1103 (Apr. 2004).
Erb et al., "Recursive deconvolution of combinatorial chemical libraries," Proc. Natl. Acad. Sci. USA, 91:11422-11426 (1994).
Ericson et al., "Studies on the sicca syndrome in patients with rheumatoid arthritis," Acta. Rheum. Scand. (1970) 16: 60-80.
Fava et al., "Transforming growth factor β1 (TGF-β1) induced neutrophil recruitment to synovial tissues: Implications for TGF-β-driven synovial inflammation and hyperplasia," The Journal of Experimental Medicine (1991) 173:1121-1132.
FDA Guidance for Industry: Estimating the Maximum Safe Starting Dose in Initial Clinical Trial for Therapeutics in Adult Healthy Volunteers, Appendix D: Converting Animal doses to human equivalent doses, Jul. 2005; 30 pgs.
Felder, et al., Diagnostic tools for hypertension and salt sensitivity testing, Current opinion in nephrology and hypertension, Jan. 2013, 22 pages.
Felici, F., "Selection of antibody ligands from a large library of oligopeptides expressed on a multivalent exposition vector," J. Mol. Biol., 222:301-310 (1991).
Felson, D.T. et al., "American College of Rheumatology Preliminary Definition of Improvement in Rheumatoid Arthritis," Arthritis Rheum. 38(6):727-735 (1995).
Ferdinand, et al., Race-based therapy for hypertension: possible benefits and potential pitfalls, Expert review of cardiovascular therapy, Nov. 2008, pp. 1357-1366.
Ferreira et al., "Nitric oxide modulates eosinophil infiltration in antigen-induced airway inflammation in rats," European Journal of Pharmacology (1998) 358: 253-259.
Ferretti et al., "Intracolonic release of nitric oxide during trinitrobenzene sulfonic acid rat colitis," Digestive Diseases and Sciences (1997) 42(12): 2606-2611.
Feutren et al., Cyclosporin Increases the Rate and Length of Remission in insulin Dependent Diabetes of Recent Onset Results of a Multicentre Double-Blind Trial, The Lancet, p. 119-124 (1986).
Fiedler, F. et al., "Purification and properties of guinea-pig submandibular-gland kallikrein," Biochem. J., 209:125-134 (1983).
Figueroa, C. D. et al., "Cellular localization of human kininogens," Agents and Actions. Supplements 38(Pt. 1):617-626 (Jan. 1992).
Final Office Action for U.S. Appl. No. 13/909,220, mailed Oct. 3, 2014, 16 pages.
Fodor et al., "Multiplexed biochemical assays with biological chips," Nature, 364:555-556 (1993).
Frank et al., "A review of antioxidants and Alzheimer's Disease," Annals of Clinical Psychiatry, 17(4):269-286 (2005).
Friberg et al., "Salivary kallikrein in Sjogren's syndrome," Clinical and Experimental Rheumatology (1988) 6:135-138.
Friedman, A. et al., "Induction of anergy or active suppression following oral tolerance is determined by antigen dosage," PNAS USA, 91:6688-6692 (Jul. 1994).
Friedman, Serum creatinine: an independent predictor of survival after stroke, Journal of internal medicine, Feb. 1991, pp. 175-179.
Fries et al., "The dimensions of health outcomes: The health assessment questionnaire, disability and pain scales," The Journal of Rheumatology (1982) 9(5):789-793.
Fuchtenbusch, M. et al., "Delay of Type 1 diabetes in high risk, first degree relatives by parenteral antigen administration: The Schwabing Insulin Prophylaxis Pilot Trial," Diabetologist, 41:536-541 (1998).

(56) References Cited

OTHER PUBLICATIONS

Fuller et al., "The cellular physiology of glandular kallikrein," Kidney International (1986) 29: 953-964.
Gallop, Mark A., et al. "Applications of combinatorial technologies to drug discovery. 1. Background and peptide combinatorial libraries." Journal of Medicinal Chemistry (1994); 37.9: 1233-1251.
Garrigue-Antar et al., "Optimisation of CCL64-based bioassay for TGF-β," Journal of Immunological Methods, (1995) 186:267-274.
GenBank Accession No. AAG11389.1, kallikrein [Mus musculus], Oct. 11, 2000, 2 pages.
GenBank Accession No. AAH05313.1, Kallikrein 1 [Homo sapiens], Nov. 3, 2006, 3 pages.
GenBank Accession No. NP113711.1, kallikrein-1 [Rattus norvegicus], Nov. 12, 2010, 3 pages.
GenBank Accession No. AAA39349 .1 National Center for Biotechnology Information, National Library of Medicine, National Institutes of Health, GenBank Locus AAA39349, Accession No. AAA39349, "Kallikrein 1 [Mus musculus domesticus]," [online]. Bethesda, MD [retrieved on Jun. 4, 2014]. Retrieved from the Internet: httn://www.ncbi.nlm.nih.gov/protein/AAA39349.1; 2 pages.
GenBank Accession No. AAI51559.1 National Center for Biotechnology Information, National Library of Medicine, National Institutes of Health, GenBank Locus AAI51599, Accession No. AAI51559; Version No. AAI51559.1 GI:154426202, [online]. Bethesda, MD [retrieved on Aug. 11, 2014]. Retrieved from the Internet: URL: http://www.ncbi.nlm.nih.gov/protein/154426202; 2 pages.
GenBank Accession No. CAE51906.1National Center for Biotechnology Information, National Library of Medicine, National Institutes of Health, GenBank Locus AE51906, Accession No. AE51906, "TPA: kallikrein 1 precursor [Rattus norvegicus]," [online]. Bethesda, MD [retrieved on Jun. 4, 2014]. Retrieved from the Internet: http://www /ncbi.nlm.nih. gov /protein/CAE51906 .1, 2 pages.
GenBank Accession No. NP 002248.1 National Center for Biotechnology Information, National Library of Medicine, National Institutes of Health, GenBank Locus NP 002248, Accession No. NP 002248, "kallikrein-1 prepoprotein [Homo sapiens]," [online]. Bethesda, MD [retrieved on Jun. 4, 2014]. Retrieved from the Internet: http://www/ncbi.nlm.nih.gov/protein/NP 002248.1; 3 pages.
GenBank: CAE51906.1, TPA: kallikrein 1 precursor [Rattus norvegicus], Apr. 25, 2006, downloaded Feb. 24, 2020, 2 pages.
Geterud et al., "Swallowing problems in rheumatoid arthritis," Acta Otolaryngol (Stockh) (1991) 111:1153-1161.
Giannoukakis, N., "Drug evaluation: BIM-51077, a dipeptidyl peptidase-IV-resistant glucagon-like peptide-1 analog," Curr. Opin. Investig. Drugs, 8(10):842-848 (2007).
Gimsa et al., "Type II collagen serology: A guide to clinical responsiveness to oral tolerance?" Rheumatol Int. (1997) 16:237-240.
Goard, C. et al., "A consolidated catalogue and graphical annotation of dbSNP polymorphisms in the human tissue kallikrein (KLK) locus," Molecular Oncology, 1:303-312 (2007).
Goodman, "Toward Evidence-Based Medical Statistics.2: The Bayes Factor," Ann Intern. Med, Jun. 15, 1999;130(12):1005-1013.
Gordon et al., "Applications of combinatorial technologies to drug discovery. 2. Combinatorial organic synthesis, library screening strategies, and future directions," J. Med. Chem., 37(10):1385-1401 (1994).
Grabley, S. et al., "8 tools for drug discovery: Natural product-based libraries," Ernst Schering Research Foundation Workshop, 32:217-252 (2000).
Graham, T.L. et al. (1977). "Characteristics of a Human Cell Line Transformed by DNA From Human Adenovirus Type 5," J. Gen. Virol., vol. 36, pp. 59-72.
Greaves et al., "Anionic salivary proteins associated with connective tissue disorders: sialated tissue kallikreins," Annals of the Rheumatic Diseases (1989) 48:753-759.
Green, B. D. et al., "Novel glucagon-like peptide-1 (GLP-1) analog (Val8)GLP-1 results in significant improvements of glucose tolerance and pancreatic β-Cell function after 3-week daily administration in obese diabetic (ob/ob) mice," The Journal of Pharmacology and Experimental Therapeutics, 318(2):914-921 (2006).
Griesbacher, T. et al., "Involvement of tissue kallikrein but not plasma kallikrein in the development of symptoms mediated by endogenous kinins in acute pancreatitis in rats," British J of Pharmacology, 137(5):692-700 (2002).
Griffiths et al., "Immunogenetic control of experimental Type II collagen-induced arthritis," Arthritis and Rheumatism (1981) 24(6): 781-789.
Guarino, M. et al., "Hepatic glutathione and nitric oxide are critical for hepatic insulin-sensitizing substance action," American Journal of Physiology—Gastrointestinal and Liver Physiology, 284:G588-G594 (2002).
Harpel, P. C., "Studies on the interaction between collagen and a plasma kallikrein-like activity," J. Clin. Invest., 51:1813-1822 (1972).
Hernandez, C. C. et al., "Kininogen-kallikrein-kinin system in plasma and saliva of patients with Sjogren's syndrome," J. Rheumatol., 25:2381-2384 (1998).
Hersch et al., "Neuroprotection for Huntington's disease: ready, set, slow," Neurotherapeutics, 5:226-236 (2008).
Hial, V. et al., "Purification and properties of a human urinary kallikrein (kininogenase)," Biochemistry, 13(21):4311-4318 (1974).
Higashi et al., "Relationship Between Insulin Resistance and Endothelium-Dependent Vascular Relaxation in Patients with Essential Hypertension," Hypertension, 29:280-285 (1997).
Holz, "Giucagoi-Like Peptide-1 Synthetic Analogs: New Therapeutic Agents for Use in the Treatment of Diabetes Mellitus," Curr. Med Chem, 10(22):2471-2483 (2003).
Houghten et al., "Drug discovery and vaccine development using mixture-based synthetic combinatorial libraries," Drug Discovery Today, 5(7):276-285 (2000).
Houghten et al., "The use of synthetic peptide combinatorial libraries for the identification of bioactive peptides," Biotechniques, 13(3):412-421 (1992).
Hsu, C. C. et al., "Five cysteine-containing compounds delay diabetic deterioration in balb/cA mice," J. Nutr., 134(12):3245-3249 (2004).
Hu, Z. Q. al., "Enhancement of lymphocyte proliferation by mouse glandular kallikrein," Immunology Letters (1992) 32:85-90.
Ibrahim et al., Elevated Serum Creatinine Predicts Higher Mortality in Stroke Patients (P3.254), Apr. 2017, 2 pages.
International Preliminary Report on Patentability for International Application No. PCT/CA2007/001321, dated Jan. 27, 2009, 8 pages.
International Preliminary Report on Patentability for International Application No. PCT/CA2008/001327, dated Jan. 26, 2010, 7 pages.
International Preliminary Report on Patentability for International Application No. PCT/CA2009/001051, dated Jan. 25, 2011, 9 pages.
International Preliminary Report on Patentability for International Application No. PCT/CA2010/000413, dated Sep. 27, 2011, 8 pages.
International Preliminary Report on Patentability for International Application No. PCT/US2018/021749, dated Sep. 10, 2019, 5 pages.
International Search Report and Written Opinion for International Application No. PCT/CA2007/001321, mailed Nov. 30, 2007, 7 pages.
International Search Report and Written Opinion for International Application No. PCT/CA2008/001327, mailed Oct. 23, 2008, 10 pages.
International Search Report and Written Opinion for International Application No. PCT/CA2009/001051, mailed Oct. 15, 2009, 14 pages.
International Search Report and Written Opinion for International Application No. PCT/CA2010/000413, mailed Jun. 7, 2010, 13 pages.
International Search Report and Written Opinion for International Application No. PCT/CA2013/050395, mailed Sep. 19, 2013, 16 pages.

(56) References Cited

OTHER PUBLICATIONS

International Search Report and Written Opinion for International Application No. PCT/CA2013/050425, mailed Oct. 4, 2013, 16 pages.
International Search Report and Written Opinion for International Application No. PCT/CA2013/050755, mailed Dec. 30, 2013, 12 pages.
International Search Report and Written Opinion for International Application No. PCT/US2012/036556, mailed Aug. 30, 2012, 15 pages.
International Search Report and Written Opinion for International Application No. PCT/US2018/021749, dated May 7, 2018, 8 pages.
Ishizaka, K., "Twenty years with IgE: From the identification of IgE to regulatory factors for the IgE response," American Association of Immunologists Presidential Address, The Journal of Immunology (1985) 135(1): i-x.
Iwata, A. et al., "Alpha-synuclein degradation by serine protease neurosin: implication for pathogenesis of synucleinopathies," Human Molecular Genetics, 12(20):2625-2635 (2003).
Jaffa, A. A. et al., "Plasma Prekallikrein: A risk marker for hypertension and nephropathy in type 1 diabetes," Diabetes, 52(5):1215-1221 (2003).
Jaffa et al., "Induction of renal kallikrein and renin gene expression by insulin and IGF-1 in the diabetic rat," Diabetes, 1997;46:2049-2056.
James, M. N. et al., "Amino acid sequence alignment of bacterial and mammalian pancreatic serine proteases based on topological equivalences," Can. J. Biochem., 56(6):396-402 (1978).
Jensen et al., "Salivary acidic proline-rich proteins in rheumatoid arthritis," Ann NY Acad Sci. (1998) 842:209-211.
Jenzano et al., "The assay of glandular kallikrein and prekallikrein in human mixed saliva," Archs Oral Biol., (1988) 33(9):641-644.
Jong, Y.-J. et al., "Human bradykinin B2 receptors isolated by receptor-specific monoclonal antibodies are tyrosine phosphorylated," Proceedings of the National Academy of Sciences of the United States of America, 90(23):10994-10998 (1993).
Junn et al., "Human alpha-synuclein over-expression increases intracellular reactive oxygen species levels and susceptibility to dopamine," Neurosci Lett., 320:146-150 (2002).
Karaca et al., "Functional pancreatic beta-cell mass: involvement in type 2 diabetes and therapeutic intervention," Diabetes Metab., 65:77-84 (2009).
Katsarou et al., "Quality of life in Parkinson's disease: Greek translation and validation of the Parkinson's disease questionnaire (PDQ-39)," Quality of Life Research, 10:159-163 (2001).
Kehrl et al., "Further studies of the role of transforming growth factor-β in human B cell function," The Journal of Immunology, (1989) 6:1868-1874.
Kehrl et al., "Transforming growth factor-β suppresses human B lymphocyte Ig production by inhibiting synthesis and the switch from the membrane form to the secreted form of Ig mRNA," The Journal of Immunology (1991) 146:4016-4023.
Kellermann, Jr. et al., "Human urinary kallikrein-amino acid sequence and carbohydrate attachment sites," Protein Seq Data Anal., Feb. 1988; 1(3):177-182.
Kelly et al., "Decreased salivary epidermal growth factor in rheumatoid disease: a possible mechanism for increased susceptibility to gastric ulceration," Brit. Med. J., (1990) 301:422-423.
Kemp et al., "Inhibition of interleukin I activity by a factor in submandibular glands of rats," The Journal of Immunology (1986) 137(7):2245-2251.
Kemp et al., "Suppression and enhancement of in vitro lymphocyte reactivity by factors in rat submandublar gland extracts," Immunology (1985) 56:261-267.
Kerby et al., "Salivary kallikrein levels in normal and in rheumatoid individuals," J Lab Clin Med. (1968) 71(4):704-708.
Kim, J. K. et al., "Multiple sclerosis: An Important Role for Post-Translational Modifications of Myelin Basic Protein in Pathogenesis," Molecular and Cellular Proteomics, 2:453-462 (2003).
Kim, Y. et al., "Identification of Hnrph3 as an autoantigen for acute anterior uveitis," Clinical Immunology, 138:60-66 (2011).
Kizer, et al., Stroke Reduction in Hypertensive Adults With Cardiac Hypertrophy Randomized to Losartan Versus Atenolol, Hypertension, Jan. 2005, pp. 46-52, vol. 45, Issue 1.
Klafki, H.-W. et al., "Therapeutic approaches to Alzheimer's disease," Brain, 129:2840-2855 (2006).
Klunk et al., "Imaging brain amyloid in Alzheimer's disease with Pittsburgh Compound-B," Ann Neural., 55:306-319 (2004).
Knoerzer et al., "Collagen-induced arthritis in the BB rat," J. Clin. Invest. (1995) 96:987-993.
Kolodka, T. et al., "Preclinical Characterization of Recombinant Human Tissue Kallikrein-1 as a Novel Treatment for Type 2 Diabetes Mellitus," (2014), PloS ONE 9(8), 8 pages.
Korbet, et al., Primary focal segmental glomerulosclerosis: clinical course and response to therapy, American journal of kidney diseases, Jun. 1994, pp. 773-783.
Kremer, J. M., "Methotrexate and emerging therapies," Rheumatic Diseases Clinics of North America (1998) 24(3):651-658.
Lam et al., "A new type of synthetic peptide library for identifying ligand-binding activity," Nature, 354:82-84 (1991).
Lampeter, E. F. et al., "The Deutsche Nicotinamide Intervention Study: An Attempt to Prevent Type 1 Diabetes," Diabetes, 47:980-984 (1998).
Larsen et al., "Individual variations of pH, buffer capacity, and concentrations of calcium and phosphate in unstimulated whole saliva," Archives of Oral Biology (1999) 44:111-117.
Lautt, W., "A new paradigm for diabetes and obesity: the hepatic insulin sensitizing substance (HISS) hypothesis," J. Pharmacol. Sci., 95(1):9-17 (2004).
Lautt, W. W. et al., "Hepatic parasympathetic (HISS) nerve-dependent control of peripheral insulin sensitivity is determined by feeding and fasting: dynamic control of HISS-dependent insulin action," American Journal of Physiology—Gastrointestinal and Liver Physiology, 281:G29-G36 (2001).
Lautt, W. W. et al., "Rapid insulin sensitivity test (RIST)," Can. J. Physiol. Pharmacol., 76:1080-1086 (1998).
Lautt, W. W., "The HISS story overview: a novel hepatic neurohumoral regulation of peripheral insulin sensitivity in health and diabetes," Canadian Journal of Physiology Pharmacology, 77:553-562 (1999).
Laxmikanthan et al., "1.70 A X-Ray Structure of Human apo Kallikrein 1: Structural Changes Upon Peptide Inhibitor/Substrate Binding," Proteins: Structure, Function, and Bioinformatics, 58:802-814 (2005).
Lee et al., "Co-stimulation of T cell proliferation by transforming growth factor-β1," The Journal of Immunology (1991) 147(4):1127-1133.
Lee, "Origins and effects of extracellular alpha-synuclein: implications in Parkinson's disease," J. Mol. Neurosci., 34:17-22 (2008).
Leger, R. et al., "Identification of CJC-1131-albumin bioconjugate as a stable and bioactive GLP-1(7-36) analog.," Bioorg. Med. Chem. Lett., 14(17):4395-4398 (2004).
Lenander-Lumikari et al., "Stimulated salivary flow rate and composition in asthmatic and non-asthmatic adults," Archives of Oral Biology, 43:151-156 (1998).
Li, H. et al., "Tissue kallikrein protects against pressure overload-induced cardiac hypertrophy through kinin B2 receptor and glycogen synthase kinase-3β activation," Cardiovascular Research, 73(1):130-142 (2007).
Li, H. et al., "Substrate specificity of human kallikreins 1 and 6 determined by phage display," Protein Science, 17:664-672 (2008).
Lin, F.-K. et al., "Molecular cloning and sequence analysis of the monkey and human tissue kallikrein genes," Biophys. Biochem. Acta, 1173:325-328 (1993).
Lindsay et al., "Inhibition of dipeptidyl peptidase IV activity by oral metformin in Type 2 diabetes," Diabetic Medicine, 22:654-657 (2005).
Little, S. P. et al., "Zyme, a novel and potentially amyloidogenic enzyme cDNA isolated from Alzheimer's disease brain," The Journal of Biological Chemistry, 272(40):25135-25142 (1997).
Liu, C-X et al., "Advances of therapy targeting at β amyloid protein in Alzheimer's disease," Chinese Journal of Clinical Rehabilitation, 7(28):3867-3869 (2003).

(56) References Cited

OTHER PUBLICATIONS

Logan and Shenk, "Adenovirus tripartite leader sequence enhances translation of mRNAs late after infection". Proc Natl Acad Sci U S A. (Jun. 1984); 81(12): 3655-3659.
Lu, H. S. et al., "Purification and characterization of human tissue prokallikrein and kallikrein isoforms expressed in Chinese hamster ovary cells," Protein Expression and Purification, Sep. 1996;8(2):227-237.
Majewska et al., "Epicutaneous immunization with myelin basic protein protects from the experimental autoimmune encephalomyelitis," Pharmalogical Reports, (2007) 59 74-79.
Manto, A. et al., "Urinary kallikrein excretion in Type 1 (insulin-dependent) diabetes mellitus," Diabetologia, 36(5):423-427 (1993).
Marras et al., "Invited article: changing concepts in Parkinson disease: moving beyond the decade of the brain," Neurology, 70(21):1996-2003 (2008).
Material Safety Data Sheet, Azo dye-impregnated collagen, Sigma-Aldrich (version 4.0), Feb. 27, 2010, 5 pages.
Mather, J.P. (1980). "Establishment and Characterization of Two Distinct Mouse Testicular Epithelial Cell Lines," Biol. Reprod., vol. 23, pp. 243-251.
Mather, J.P. et al. (1982). "Culture of Testicular Cells in Hormone-Supplemented Serum-Free Medium," Annals NY Acad. Sci., vol. 383, pp. 44-68.
Matthews et al., "Salivary secretion and connective tissue disease in man," Annals of the Rheumatic Diseases, (1985) 44: 20-26.
Mazzone, P et al., "Our new understanding of pulmonary alveolar proteinosis: What an internist needs to know," Cleveland Clinic Journal of Medicine, 68: 977-978 (2001).
McCartney-Francis et al., "Transforming growth factor β: a matter of life and death," Journal of Leukocyte Biology (1994) 55:401-409.
McCormack et al., "Molecular forms of prostate-specific antigen and the human kallikrein gene family: A new era," Urology (1995) 45(5):729-744.
McIntosh et al., "Antigen-specific suppressor macrophages induced by culture with cyclosporine A plus acetoylcholine receptor," Journal of Neuroimmunology (1989) 25:75-89.
McIntosh et al., "Tolerance to acetylcholine receptor induced by AChR-coupled syngeneic cells," Journal of Neuroimmunology (1992) 38:75-84.
Medline Plus, Type 1 Diabetes, U.S. National Library of Medicine, NIH, [online], [Retrieved on Aug. 28, 2013], [Retrieved from the Internet: URL: http://www.nlm.nih.gov/medlineplus/ency/article/000305.htm], 7 pages.
Meier, J. J., "Beta cell mass in diabetes: a realistic therapeutic target?," Diabetologia, 51(5):703-713 (2008).
Merrifield, "Solid Phase Peptide Synthesis. I. The Synthesis of a Tetrapeptide," J Am Chem Soc., 1963;85(14):2149-2154.
Miranda et al., "The amidase activity of human tissue kallikrein is significantly higher in the urine of patients with either type 1 or gestational diabetes mellitus," Int. J. Diabetes & Metab., 18:124-131 (2010).
Montanari, D. et al., "Kallikrein gene delivery improves serum glucose and lipid profiles and cardiac function in streptozotocin-induced diabetic rats," Diabetes, 54:1573-1580 (2005).
Moore, M. C. et al., "Effect of hepatic denervation on peripheral insulin sensitivity in concious dogs," American Journal of Physiology—Endocrinology and Metabolism, 282:E286-296 (2002).
Moreau, M. E. et al., "The kallikrein-kinin system: current and future pharmacological targets," Journal of Pharmacological Sciences, Sep. 2005;99(1):6-38.
Morris et al., "Hapten-induced model of chronic inflammation and ulceration in the rat colon," Gastroenterology (1989) 96:795-803.
Moser, A. et al., "Beta cell antigens in type 1 diabetes: triggers in pathogenesis and therapeutic targets," F1000 Biology Reports 2010, 2:75 (doi:10.3410/B2-75), 4 pages.
Nagy, E. et al., "Immunoregulatory effects of glandular kallikrein from the salivary submandibular gland of rats," Neuroimmunomodulation (1997) 4:107-112.

Nandhagopal et al., "Functional imaging in Parkinson disease," Neurology, 70:1478-1488 (2008).
Naslund, E. et al., "Glucagon-like peptide-1 analogue LY315902: effect on intestinal motility and release of insulin and somatostatin," Regul. Pept., 106(1-3):89-95 (2002).
Nathan, D. M. et al., "Medical Management of Hyperglycemia in Type 2 Diabetes: A Consensus Algorithm for the Initiation and Adjustment of Therapy," Diabetes Care, 32(1):193-203 (2009).
Nathan, et al., Diabetes Control and Complications Trial Research Group, "The Effect of Intensive Treatment of Diabetes on the Development and Progression of Long-Term Complications in Insulin-Dependent Diabetes Mellitus." The New England Journal of Medicine, Sep. 30, 1993, 977-986.
Naughton, M. A. et al., "Esteropeptidase and thymotropic activity of a protein isolated from the mouse submaxillary gland," Biochimica et Biophysica Acta (1972) 263:106-114.
NCBI Reference Sequence: NP 001003262.1, Feb. 22, 2013, 2 pages.
NCBI Reference Sequence: XP _003916022.1, Sep. 4, 2012, 2 pages.
NCBI Reference Sequence: XP_003997527.1, Nov. 6, 2012, 2 pages.
Neef et al., "Dementia with Lewy bodies: an emerging disease," Am. Fam. Physician, 73:1223-1229 (2006).
Noble et al., "Inhibition of glycogen synthase kinase-3 by lithium correlates with reduced tauopathy and degeneration in vivo," Proc. Natl. Acad. Sci. USA, 102(19):6990-6995 (2005).
Non-Final Office Action for U.S. Appl. No. 13/909,220, mailed May 15, 2014, 16 pages.
Norris, S. L. et al., "Drug class review: Newer drugs for the treatment of diabetes mellitus," Final Report, Aug. 2008, Oregon Health & Science University, Portland, Oregon, 2008, 99 pages.
Ole-Moiyoi et al., "Structural studies of a human urinary kallikrein (urokallikrein)," PNAS, Jul. 1979;76(7):3121-3125.
Origene, "KLK1 (NM_002257) Human cDNA Clone," [online], [Retrieved on Feb. 18, 2012], [Retrieved from the Internet: URL: http://www.origene.com/human_cdna/NM_002257/SC122623/KLK1.aspx], 1 page.
Ottlecz, A. et al., "Plasmakinin system in alloxan diabetic rats," Adv. Biosci., 17:57-63 (1978).
Periquet et al., "Aggregated alpha-synuclein mediates dopaminergic neurotoxicity in vivo," J Neurosci., 27:3338-46 (2007).
Perris, A. D., et al., "The mitogenic action of bradykinin on thymic lymphocytes and its dependence on calcium," Proc. Soc. Exp. Biol. Med., 130:1198-1201 (1969).
Pizard, A. et al., "Genetic deficiency in tissue kallikrein activity in mouse and man: effect on arteries, heart and kidney," Biological Chemistry, 389(6):701-706 (2008).
Pratt, Central role for ENaC in development of hypertension, Journal of the American society of nephrology, Nov. 2005, pp. 3154-3159.
Pratt, et al., Racial difference in the activity of the amiloride-sensitive epithelial sodium channel, Hypertension, Dec. 2002, pp. 903-908.
Predki, P. et al., "Protein microarrays: A new tool for profiling antibody cross-reactivity," Human Antibodies, 14:7-15 (2005).
Proud et al., "Kinins are generated in vivo following nasal airway challenge of allergic individuals with allergen," J. Clin. Invest. (1983) 72:1678-1685.
Rader, C., "Antibody libraries in drug and target discovery," Drug Discovery Today, 6(1):36-43 (2001).
Recombinant Human Kallikrein-1/ KLK1. Datasheet [online] SinoBiological Inc., 2011 [retrieved on Aug. 14, 2013]. [Retrieved from the Internet: URL: http://web.archive.org/web/20110911225357/http://www.sinobiological.com/KLK1-Protein-g-284.html]; 4 pages.
Reibman et al., "Transforming growth factor β1, a potent chemoattractant for human neutrophils, bypasses classic signal-transduction pathways," Proc. Natl. Acad. Sci. (1991) 88:6805-6809.
Reidy, et al., Genetic risk of APOL1 and kidney disease in children and young adults of African ancestry, Current opinion in pediatrics, Apr. 2018 Apr.;30(2):252.
Response to Non-Final Office Action for U.S. Appl. No. 13/909,220, filed Aug. 15, 2014, 14 pages.

(56) References Cited

OTHER PUBLICATIONS

Richards, R. I. et al., Mouse glandular kallikrien genes, The Journal of Biological Chemistry, 257(6):2758-2761 (1982).
Roberts et al., "New class of transforming growth factors potentiated by epidermal growth factor: Isolation from non-neoplastic tissues," Proc. Natl. Acad. Sci. (1981) 78(9):5339-5343.
Roberts et al., "The transforming growth-factor-βs," Handbook of Pharmacology 95(1990):Chapter 8:419-472.
Robinson et al., "Transfer of human serum IgG to nonobese diabetic Igμ$^{null}$ mice reveals a role for autoantibodies in the loss of secretory function of exocrine tissues in Sjogren's syndrome," Proc. Natl. Acad. Sci. (1998) 95: 7538-7543.
Rosenberg, et al., Focal segmental glomerulosclerosis, Clinical journal of the American Society of Nephrology: CJASN, Mar. 2017, 31 pages.
Rothschild, A. M. et al., "Increased kininogen levels observed in plasma of diabetic patients are corrected by the administration of insulin," Hormone and Metabolic Research, 31(5):326-328 (1999).
Rowe, M. K. et al., "GSK-3 is a viable potential target for therapeutic intervention in bipolar disorder," Neuroscience and Biobehavioral Reviews, 31(6):920-931 (2007).
Russell et al., "Investigation of xerostomia in patients with rheumatoid arthritis," JADA (1998) 129: 733-739.
Rust, et al., Mutagenically separated PCR (MS-PCR): a highly specific one step procedure for easy mutation detection, Nucleic Acids Research, Aug. 1993, pp. 3623-3629,.
Rydel, et al., Focal segmental glomerular sclerosis in adults: presentation, course, and response to treatment, American Journal of Kidney Diseases, Apr. 1995, pp. 534-542.
Sabbadini et al., "The submandibular gland: A key organ in the neuro-immuno-regulatory network?" Neuroimmunomodulation, 2:184-202 (1995).
Sagara, T. et al., "Reduction of collagen type 1 in the ciliary muscle of inflamed monkey eyes," Investigative Ophthalmology & Visual Science, 40:2568-2576 (1999).
Salgame et al., "Differing lymphokine profiles of functional subsets of human CD4 and CDS cell clones," Science (1991) 254 (5029): 279-282.
Sarno, et al., In vivo regulation of GSK3 phosphorylation by cholinergic and NMDA receptors, Neurobiology of Aging, Mar. 2006, pp. 413-422, vol. 27, Issue 3.
Sartor et al., "Selective kallikrein-kinin system activation in inbred rats differentially susceptible to granulomatous enterocolitis," Gastroenteroloy (1996) 110:1467-1481.
Schapira et al., "Mitochondria in the aetiology and pathogenesis of Parkinson's disease," Lancet Neurol., 7:97-109 (2008).
Schlebusch, et al., Tales of human migration, admixture, and selection in Africa., Annual Review of Genomics and Human Genetics, Aug. 2018, pp. 405-428.
Scott J.K., et al., "Searching for Peptide Ligands with an Epitope Library," Science, Jul. 27, 1990, vol. 249, No. 4967, pp. 386-390, Retrieved from URL: http://www.jstor.org.
Shaw, J. et al., "Regulation of human tissue kallikrein-related peptidase expression by steroid hormones in 32 cell lines," Biological Chemistry, 389(11):1409-1419 (2008).
Shi, R. et al., "Tissue Kallikrein Alleviates Cerebral Ischemia-Reperfusion Injury by Activating the B2R-ERK1/2-CREB-Bcl-2 Signaling Pathway in Diabetic Rats," Oxidative Medicine and Cellular Longevity, vol. 2016, Article ID 1843201, pp. 1-14 (2016).
Shimoke et al., "Nerve growth factor prevents 1-methyl-4-phenyl-1,2,3,6-tetrahydropyridine-induced cell death via the Akt pathway by suppressing caspase-3-like activity using PC12 cells: relevance to therapeutical application," J. Neurosci. Res., 63(5):402-409 (2001).
Simon, et al., Bartter's syndrome, hypokalaemic alkalosis with hypercalciuria, is caused by mutations in the Na—K—2Cl cotransporter NKCC2, Nature genetics, Jun. 1996, 183-8.
Simson, J. A. V. et al., "Histopathology of lymphatic tissue in transgenic mice expressing human tissue kallikrein gene," Lab. Invest., 71(5):680-687 (1994).
Simson, J. A. V., "Localization of kallikrein gene family proteases in rat tissues," Agents and Actions-Suppl., 38(1):595 (1992).
Slim, R. et al., "Loss-of-function polymorphorphism of the human kallikrein gene with reduced urinary kallikrein activity," J. Am. Soc. Nephrol., 2002; 13:968-976.
Song et al., "The thymus plays a role in oral tolerance in experimental autoimmune encephalomyelitis," The Journal of immunology (2006) 177:1500-1509.
Song, G. et al., "New Centromere Autoantigens Identified in Systemic Sclerosis Using Centromere Protein Microarrays," Journal of Rheumatology, 40:461-468 (2013).
Spinetti, G. et al., "Tissue kallikrein is essential for invasive capacity of circulating proangiogenic cells," Circulation Research, 108(3):284-293, Feb. 2011.
Steinbrocker et al., "Therapeutic criteria in rheumatoid arthritis," The Journal of the American Medical Association (1949) 140(8):659-662.
Stone, et al., "Critical Role of Tissue Kallikrein in Vessel Formation and Maturation". Arteriosclerosis Thromb Vase Biol. (2009); 29(5): 657-664.
Su et al., "Lithium, a common drug for bipolar disorder treatment, regulates amyloid-β precursor protein processing," Biochemistry, 43(22):6899-6908 (2004).
Sullivan, et al., "Impairment of lachrymal and salivary secretion and cellular immune responses to salivary antigens in rheumatoid arthritis", Ann. Rheum. Dis. (1978); 37(2): 164-167.
Sun, H. et al., "Prolonged hypotensive effect of human tissue kallikrein gene delivery and recombinant enzyme administration in spontaneous hypertension rats," Experimental and Molecular Medicine, 36(1):23-27 (2004).
Sung, J. et al., "Proteolytic cleavage of extracellular secreted α-synuclein via matrix metalloproteinases," Journal of Biological Chemistry, 280(26):25216-25224 (2005).
Supplemental European Search Report for European Application No. 10755352.1, mailed Nov. 13, 2012, 9 pages.
Supplementary European Search Report for European Application No. 07784988.3, mailed Sep. 17, 2009, 7 pages.
Supplementary European Search Report for European Application No. 08783241.6, mailed Feb. 22, 2012, 7 pages.
Supplementary European Search Report for European Application No. 09799910.6, mailed Aug. 9, 2012, 8 pages.
Supplementary European Search Report for European Application No. 13801165.5, mailed Feb. 8, 2016, 8 pages.
Swant, Catalog listing for Monoclonal anti Rat Renin (118), [online], [Retrieved on Jan. 31, 2005], [Retrieved from the Internet: URL: http://www.swant.com/Antibodies_renin.htm, 1 page.
Swift, G. H. et al., "Rat pancreatic kallikrein mRNA: Nucleotide sequence and amino acid sequence of the encoded preproenzyme," Proc. Nat. Acad. Sci. U.S.A., 79:7263-7267 (1982).
No Author, Synopsis "Type 2 Diabetes: Insulin Resistance May Be the Result of Mitochondrial Dysfunction.," PLOS Med 2(9): e292, 2 pages (2005).
Szodoray, P. et al., "Anti-citrullinated protein/peptide autoantibodies in association with genetic and environmental factors as indicators of disease outcome in rheumatoid arthritis," Autoimmunity Reviews, 9:140-143 (2010).
Takada, K. et al., "Autoimmunity against a tissue kallikrein in IQI/Jic mice: a model for Sjogren's syndrome," J. Biol. Chem., 280:3982-3988 (2005).
Takayama et al., "Characterization of the precursor of prostate-specific antigen," The Journal of Biological Chemistry (1997) 272(34):21582-21588.
Teitelbaum et al., "Immunomodulation of experimental autoimmune encephalomyelitis by oral administration of copolymer I," Proc. Natl. Acad. Sci. USA (1999) 96: 3842-3847.
Tetzlaff et al., "CHIP targets toxic alpha-Synuclein oligomers for degradation," J. Biol. Chem., 283:17962-17968 (2008).
Teva, "Copaxone (glatiramer acetate injection)," [online], [Retrieved on the internet: URL: http://www.msakc.org/Articles/Copaxone.htm, [Retrieved on Jul. 31, 2008], 4 pages.
Teva Pharmaceutical Industries Ltd., "Copaxone (glatiramer acetate injection)," Package Insert (May 2007), 4 pages.

(56) References Cited

OTHER PUBLICATIONS

Thorkildsen, C. et al., "Glucagon-like peptide 1 receptor agonist ZP10A increases insulin mRNA expression and prevents diabetic progression in db/db mice," The Journal of Pharmacology and Experimental Therapeutics, 307(2):490-496 (2003).

Thorne et al., "Delivery of insulin-like growth factor-I to the rat brain and spinal cord along olfactory and trigeminal pathways following intranasal administration," Neuroscience, 127(2):481-496 (2004).

Tian, L. et al., "Reversal of New-Onset Diabetes through Modulating Inflammation and Stimulating β-Cell Replication in Nonobese Diabetic Mice by a Dipeptidyl Peptidase IV Inhibitor," Endocrinology, Jul. 2010, 151(7):3049-3060.

Tishkoff, et al., The genetic structure and history of Africans and African Americans, Science, May 2009, pp. 1035-1044.

Tofaris et al., "Pathological changes in dopaminergic nerve cells of the substantia nigra and olfactory bulb in mice transgenic for truncated human alpha-synuclein(1-120): implications for Lewy body disorders," J. Neurosci., 26:3942-3950 (2006).

Trautschold, I., "Assay methods in the kinin system," Handbook of Experimental Pharmacology (1970) 25: 52-81.

Trentham, D. E., "Oral tolerization as a treatment of the rheumatoid arthritis," Rheumatic Diseases Clinics of North America (1998) 24 (3): 525-536.

Tschetsche, H. et al., "The primary structure of porcine gladular kallikreins," Adv. Exp. Med. Biol., 120A:245-260 (1979).

Tschope et al., "Functional, biochemical, and molecular investigations of renal kallikrein-kinin system in diabetic rats," Am. J. Physiol. Heart Circ. Physiol., 277:H2333-H2340 (1999).

Turner, A. J. et al., "Targeting amyloid-degrading enzymes as therapeutic strategies in neurodegeneration," Ann. N.Y. Acad. Sci., 1035:1-20 (2004).

Uehara, S. et al., "Kallikrein-kinin system in diabetic patients," Drug. Res., 38(5):721-723 (1988).

UniProtKB/Swiss-Prot Accession No. P06870; May 14, 2014, 11 pages [Retrieved from the internet: URL: www.uniprot.org/uniprot/P06870], [Retrieved on May 3, 2014].

Urlaub et al., "Isolation of Chinese hamster cell mutants deficient in dihydrofolate reductase activity," Proc. Natl. Acad. Sci. USA, 1980, 77(7), pp. 4216-4220.

Vickers, J. C., "A vaccine against Alzheimer's disease," Drugs Aging, 19(7):487-494 (2002).

Vojdani et al., "Methyl tertiary-butyl ether antibodies among gasoline service station attendants," Ann. NY Acad. Sci., 837:96-104 (1997) (Abstract).

Wahl et al., "Transforming growth factor type β induces monocyte chemotaxis and growth factor production," Proc. Natl. Acad. Sci. (1987) 84: 5788-5792.

Wahl, S. M., "Transforming growth factor beta (TGF-β) in inflammation: A cause and a cure," Journal of Clinical Immunology (1992) 12(2):61-74.

Wahren, J. et al., "Role of C-peptide in human physiology," Am. J. Physiol. Endocrinol. Metab., 278(5): E759-E768 (2000).

Walker et al., "Interaction of human IgG chimeric antibodies with the human FcRI and FcRII receptors: Requirements for antibody-mediated host cell-target cell interaction," Molecular Immunology, 26(4):403-411 (1989).

Wang, et al., Global, regional, and national life expectancy, all-cause mortality, and cause-specific mortality for 249 causes of death, 1980-2015: a systematic analysis for the Global Burden of Disease Study 2015, The lancet, Oct. 2016, pp. 1459-1544.

Wang et al., "Investigation of the clinical value of total saliva flow rates," Archives of Oral Biology (1998) 43:39-43.

Wascher et al., "Effects of low dose L-arginine on insulin-mediated vasodilatation and insulin sensitivity," Eur. J. Clin. Invest. 27:690-695 (1997).

Weinblatt et al., "Efficacy of low-dose methotrexate in rheumatoid arthritis," The New England Journal of Medicine (1985) 312(13):818-822.

Weiner, H.L., "Oral tolerance with Copolymer 1 for the treatment of multiple sclerosis," Proc. Natl. Acad. Sci. USA (1999) 96: 3333-3335.

Weir et al., "Five Stages of Evolving β-Cell Dysfunction During Progression to Diabetes," Diabetes, 53(3):S16-S21 (2004).

Wikipedia, "Kidney" [online], [Retrieved on Jan. 31, 2005], [Retrieved from the Internet: URL: http://www.wikipedia.org/wiki/Kidney], 5 pages.

Wilson, R. D. et al., "Fructose-fed streptozotocin-injected rat: an alternative model for type 2 diabetes," Pharmacological Reports, v.64, pp. 129-139 (2012).

Wines, D. R. et al., "Organization and expression of the rat kallikrein gene family," J. Biol. Chem., 264(13):7653-7662 (1989).

Wolinsky, J.S., "The use of glatiramer acetate in the treatment of multiple sclerosis," Adv. Neural. (2006) 98:273-92 (Abstract).

Xia et al., "Kallikrein Protects Against Ischemic Stroke by Inhibiting Apoptosis and inflammation and Promoting Angiogenesis and Neurogenesis," Human Gene Ther. 17:206-219 (2006).

Xia et al., "Postischemic brain injury is exacerbated in mice lacking the kinin B2 receptor," Hypertension, 47(4):752-761 (2006).

Yamamura et al., "Defining protective responses to pathogens: Cytokine profiles in leprosy lesions," Science (1991) 254 (5029):277-279.

Yan et al., "Matrix metalloproteinase-9 degrades amyloid-β fibrils in Vitro and compact plaques in Situ," Journal of Biological Chemistry, 281(34):24566-24574 (2006).

Yao et al., "Tissue kallikrein infusion prevents cardiomyocyte apoptosis, inflammation and ventricular remodeling after myocardial infarction," Regulatory Peptides, 140(1-2):12-20 (2007).

Yao, Y. et al., "Tissue kallikrein promotes neovascularization and improves cardiac function by the Akt-glycogen synthase kinase-3β pathway," Cardiovascular Research, 80(3):354-364 (2008).

Yin et al., "Kallikrein/kinin protects against myocardial apoptosis after ischemia/reperfusion via akt-glycogen synthase kinase-3 and Akt-Bad-14-3-3 signaling pathways," The Journal of Biological Chemistry, 280(9):8022-8030 (2005).

Yki-Jarvinen, "Combination Therapies with Insulin in Type 2 Diabetes," Diabetes Care, 24(4):758-767 (2001).

Yost et al., "Tandem quadrupole mass spectrometry," In: Tandem Mass Spectrometry, McLafferty (Ed.), Wiley & Sons, New York, pp. 175-194 (1983).

Yousef, G. et al., "Genomic organization of the human kallikrein gene family on chromosome 19q13.3-q13.4," Biochemical and Biophysical Research Communications, 276(1):125-133 (2000).

Yousef, G. et al., "In-silico analysis of kallikrein gene expression in pancreatic and colon cancers," Anticancer Research, 24(1):43-51 (2004).

Yousef, G. M. et al., "Molecular cloning of the human kallikrein 15 gene (KLK15)," J. Biol. Chem., 276(1):53-61 (2001).

Yousef, G. M. et al., "Role of kallikrein enzymes in the central nervous system," Clinica Chimica Acta, 329(1-2):1-8 (2003).

Yousef, G. M. et al., "The new human tissue kallikrein gene family: structure, function, and association to disease," Endocrine Reviews (Apr. 2001); 22(2): 184-204.

Yuan, G. et al., "Tissue Kallikrein Reverses Insulin Resistance and Attenuates Nephropathy in Diabetic Rats by Activation of Phosphatidylino sitol 3-Kinase/Protein Kinase B and Adenosine 5-Monophosphate-Activated Protein Kinase SiQnalinQ Pathways," Endocrinology, 148(5):2016-2026 (2007).

Zhang, et al., Polymorphisms in CYP11B2 and CYP11B1 genes associated with primary hyperaldosteronism, Hypertension Research, May 2010, pp. 478-484.

Zhao et al., "A coding polymorphism of the kallikrein 1 gene is associated with essential hypertension: a tagging SNP-based association study in a Chinese Han population," J. Hypertens., 25:1821-1827 (2007).

Zhao et al., "Gene therapy with human tissue kallikrein reduces hypertension and hyperinsulinemia in fructose-induced hypertensive rats," Hypertension, 42:1026-1033 (2003).

Zheng et al., "Amyloid β peptide induces tau phosphorylation and loss of cholinergic neurons in rat primary septal cultures," Neuroscience, 115(1):201-211 (2002).

Affidavit of Harry Alcorn, Jr., dated Jul. 25, 2023, 5 pages.

(56) References Cited

OTHER PUBLICATIONS

Bork, et al., "Increasing the sialylation of therapeutic glycoproteins: the potential of the sialic acid biosynthetic pathway," J Pharm Sci. Oct. 2009; 98(10):3499-508.

Capes, S.E., et al., "Stress hyperglycemia and prognosis of stroke in nondiabetic and diabetic patients: a systematic overview," Stroke. Oct. 2001; 32(10):2426-32.

Chao, et al., "The tissue kallikrein-kinin system protects against cardiovascular and renal diseases and ischemic stroke independently of blood pressure reduction," Biol Chem. Jun. 2006; 387(6):665-75.

Choi, Y., et al., "Predicting the functional effect of amino acid substitutions and indels," PLoS One. 2012; 7(10):e46688, 13 pages. Epub Oct. 8, 2012.

Co-pending U.S. Appl. No. 18/295,991 inventor Rick Pauls et al., filed Apr. 5, 2023, 36 pages.

DiaMedica Therapeutics, DiaMedica Therapeutics Doses First Patient in Phase 1 b Clinical Study of DM199 in Patients with Chronic Kidney Disease. Press Release (online). Feb. 14, 2019 [retrieved on Jun. 17, 2023]. Retrieved from the Internet: https://www.diamedica.com/investors/press-releases/detail/1566/diamedica-therapeutics-doses-first-patient-in-phase-1b; 3 pages total: p. 1, 1st and 4th paragraphs; p. 3, 2nd paragraph.

Extended European Search Report for European Patent Application No. EP 18763243.5 dated Jan. 18, 2021, 8 pages.

Friedman, P., "Predictors of survival after cerebral infarction: importance of cardiac factors," Aust N Z J Med. Feb. 1994; 24(1):51-4.

Guettier, S., et al., "Factors associated with timing of early neurological improvement after thrombolysis for ischaemic stroke," Eur J Neurol. Mar. 2016; 23(3):664-7. Epub Jan. 20, 2016.

Guo et al., "Protein tolerance to random amino acid change," Proc Natl Acad Sci USA. Jun. 22, 2004; 101(25): 9205-10. Epub Jun. 14, 2004.

International Preliminary Report on Patentability for International Application No. PCT/CA2013/050395, dated Nov. 25, 2014, 10 pages.

International Preliminary Report on Patentability for International Application No. PCT/CA2013/050425, dated Dec. 9, 2014, 10 pages.

International Search Report and Written Opinion for PCT Application No. PCT/US2023/065385 dated Aug. 1, 2023, 18 pages.

Lu, H. S. et al., "Human urinary kallikrein: complete amino acid sequence and sites of glycosylation," Int. J Peptide Protein Res., 1989; 33:237-249.

Matthews, B. W., "Structural and genetic analysis of protein stability," Annu. Rev. Biochem., 62:139-160 (1993).

Naicker, et al., "Tissue kallikrein and kinins in renal disease," Immunopharmacology, Oct. 1999, pp. 183-192.

NCBI Reference Sequence: XP_004061305.1, Dec. 3, 2012, 1 page.

Ng and Henikoff, "Predicting the Effects of Amino Acid Substitutions on Protein Function," Annu Rev Genomics Hum Genet. (2006); 7:61-80.

Watson, E. et al., "Comparison of N-linked oligosaccharides of recombinant human tissue kallikrein produced by Chinese hamster ovary cells on microcarrier beads and in serum-free suspension culture," Biotechnol. Prog., Jan.-Feb. 1994;10(1):39-44.

Yang, Q. et al., "Purification of human tissue prokallikrein excreted from insect cells by liquid chromatography," J Pharm Biomed Anal., Sep. 15, 2005; 39(3-4):848-852.

Yu, et al., "Association of the tissue kallikrein gene promoter with ESRD and hypertension," Kidney International, vol. 61 (2002), pp. 1030-1039.

Miao, et al., "Exogenous human urinary kallidinogenase increases cerebral blood flow in patients with acute ischemic stroke," Neurosciences (Riyadh). Apr. 2016; 21(2):126-30.

International Preliminary Report on Patentability for International Application No. PCT/US2023/065385, dated Oct. 17, 2024, 7 pages.

* cited by examiner

| Cohort | Patients N | Day -1 FBG¹ (mmol/L) | ΔFBG Mean | 95% CI |
|---|---|---|---|---|
| Placebo | 12 | 9.48 (1.2) | -0.927 | (-2.019, 0.164) |
| Low 3 µg/kg | 13 | 10.425 (2.1) | -0.925* | (-1.743, -0.107) |
| High 15 µg/kg | 12 | 10.458 (1.5) | -0.025 | (-0.651, 0.601) |

¹Mean (SD)     *P<0.05

Figure 1

DOSAGE FORMS OF TISSUE KALLIKREIN 1

CROSS-REFERENCE TO RELATED APPLICATIONS

This application is a divisional of U.S. application Ser. No. 16/492,059, filed Sep. 6, 2019, which is a U.S. National Stage Application under 35 U.S.C. § 371 of International Application No. PCT/US2018/021749, filed Mar. 9, 2018, which claims priority under 35 U.S.C. § 119(e) to U.S. Provisional Application No. 62/567,406, filed Oct. 3, 2017; U.S. Provisional Application No. 62/516,463, filed Jun. 7, 2017; and U.S. Provisional Application No. 62/469,385, filed Mar. 9, 2017, each of which is incorporated by reference in its entirety.

STATEMENT REGARDING SEQUENCE LISTING

The Sequence Listing XML associated with this application is provided in XML file format and is hereby incorporated by reference into the specification. The name of the XML file containing the Sequence Listing XML is DIAM_037_04 US_ST26.xml. The XML file is about 5,452 bytes, was created on Nov. 3, 2023, and is being submitted electronically via USPTO Patent Center.

BACKGROUND

Technical Field

Embodiments of the present disclosure relate to dosage forms of one or more tissue kallikrein-1 (KLK1) polypeptides which have a total KLK1 polypeptide dosage of about 0.1 µg/kg to about 10.0 µg/kg, including subcutaneous and intravenous dosage forms. Also provided are related devices and methods of use thereof, for example, for treating ischemic and hemorrhagic conditions.

Description of the Related Art

Tissue kallikreins all possess protease activity with a substrate specificity similar to that of trypsin or chymotrypsin. The most well-characterized activity of KLK1 is its enzymatic cleavage of kininogen to produce bradykinin (BK)-like peptides, collectively known as kinins, which activate, either directly or indirectly, subtypes of both bradykinin receptors (BK-B1, BK-B2). Activation of BK receptors by kinins set in motion a large number of complex metabolic pathways in response to ischemia within the body, which can include improved blood flow (through vasodilation), an anti-inflammatory response, cell repair through angiogenesis or vasculogenesis, and decrease of apoptosis. There is a significant body of scientific studies which show that tissue kallikrein-mediated release increases blood flow in a variety of tissues including kidney and heart (see, e.g., Stone et al., Arterioscler Thromb Vasc Biol. 29: 657-664, 2009), and that such is likely one mode by which kallikrein treatment addresses certain conditions. It is therefore believed that KLK1 has the potential to treat a broad spectrum of clinical scenarios where re-establishing blood flow and reducing inflammation in patients is vital to preserving organ function, including brain, kidney, and heart function. However, there remains a need to identify optimal dosage forms and routes of administration that achieve and maintain therapeutic levels of KLK1 in humans. The present disclosure address these and other needs.

BRIEF SUMMARY

Embodiments of the present disclosure relate to the unexpected discovery that formulations of tissue kallikrein-1 (KLK1) have an inverse dose curve, where up to a certain point administration of lower-dosage formulations show an improved pharmacokinetic and/or activity profile relative to higher-dosage formulations.

Certain embodiments therefore include a dosage form comprising one or more tissue kallikrein (KLK1) polypeptides which are formulated at a total KLK1 polypeptide dosage of about 1.0 µg/kg to about 5.0 µg/kg or to about 10 µg/kg. In certain embodiments, the dosage form is suitable for subcutaneous or intravenous administration.

In some embodiments, the dosage form comprises a total KLK1 polypeptide dosage of about 0.1, 0.2, 0.3, 0.4, 0.5, 0.6, 0.7, 0.75, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10 µg/kg, including all ranges in between.

Particular dosage forms comprise a total KLK1 polypeptide subcutaneous dosage form of about 1.0 to about 4.0 µg/kg, or about 1.0 to about 3.0 µg/kg, or about 1.0 to about 2.0 µg/kg, or about 2.0 to about 5.0 µg/kg, or about 2.0 to about 4.0 µg/kg, or about 2.0 to about 3.0 µg/kg, or about 3.0 to about 5.0 µg/kg, or about 3.0 to about 4.0 µg/kg, or about 2.5 to about 3.5 µg/kg, or about 3 µg/kg.

Particular dosage forms comprise a total KLK1 polypeptide intravenous dosage form of about 0.5 µg/kg to about 3.0 µg/kg, or about 0.5 µg/kg to about 2.0 µg/kg, or about 0.5 µg/kg to about 1.0 µg/kg, or about 0.5 µg/kg to about 0.8 µg/kg, or about 0.5 µg/kg to about 0.75 µg/kg, or about 0.75 µg/kg.

Some dosage forms comprise a mixture of KLK1 glycoforms, for example, a first KLK1 polypeptide and a second tissue KLK1 polypeptide:
  wherein the first KLK1 polypeptide has three glycans attached at three different positions per polypeptide and the second KLK1 polypeptide has two glycans attached at two different positions per polypeptide; and
  wherein the first KLK1 polypeptide and the second KLK1 polypeptide are present in the dosage form at a ratio of about 45:55 to about 55:45.

In some aspects, one or more of the glycans are N-linked glycans. In some aspects, one or more of the glycans are attached at amino acid residues 78, 84, or 141 of KLK1 as defined by SEQ ID NO: 3 or 4. In some aspects, the three glycans of the first KLK1 polypeptide are N-linked glycans at residues 78, 84, and 141. In some aspects, the two glycans of the second KLK1 polypeptide are N-linked glycans at residues 78 and 84 but not 141. In some aspects, the first KLK1 polypeptide and the second KLK1 polypeptide are present in the dosage form at a ratio of about 50:50.

Some dosage forms comprise a mixture of a triple glycoform of a KLK1 polypeptide and a double glycoform of a KLK1 polypeptide, wherein the triple glycoform and the double glycoform are present in the dosage form at a ratio of about 45:55 to about 55:45. In some aspects, the triple glycoform includes N-linked glycans at amino acid residues 78, 84, and 141 of KLK1, as defined by SEQ ID NO: 3 or 4. In some aspects, the double glycoform includes N-linked glycans at amino acid residues 78 and 84, but not at amino acid residue 141 of KLK1, as defined by SEQ ID NO: 3 or 4. In some aspects, the triple glycoform and the double glycoform are present in the dosage form at a ratio of about 50:50.

In certain embodiments, the one or more KLK1 polypeptide(s) are mature KLK1 polypeptides, human KLK1 (hKLK1) polypeptides, or mature hKLK1 polypeptides, including any combination thereof (for example, SEQ ID NO:3 or 4 and variants thereof).

In some embodiments, the hKLK1 polypeptide(s) comprise, consist, or consist essentially of amino acid residues 78-141 of SEQ ID NO:1 or amino acids residues 78-141 SEQ ID NO:2, or an active fragment thereof, or an active variant having at least about 90, 95, 96, 97, 98, or 99% sequence identity to amino acid residues 78-141 of SEQ ID NO:1 or amino acids residues 78-141 SEQ ID NO:2.

In some embodiments, the hKLK1 polypeptide(s) comprise, consist, or consist essentially of amino acid residues 25-262 of SEQ ID NO: 1 or amino acid residues 25-262 of SEQ ID NO:2, or an active fragment thereof, or an active variant having at least about 90, 95, 96, 97, 98, or 99% sequence identity to amino acid residues 25-262 of SEQ ID NO: 1 or amino acid residues 25-262 of SEQ ID NO:2.

In some embodiments, the KLK1 polypeptide(s) comprise an amino acid sequence having at least about 90, 95, 96, 97, 98, or 99% sequence identity to amino acid residues 25-262 of SEQ ID NO:2, and wherein the KLK1 polypeptide(s) comprises E145 and/or A188. In some embodiments, the KLK1 polypeptide(s) comprise an amino acid sequence having at least about 90, 95, 96, 97, 98, or 99% sequence identity to amino acid residues 25-262 of SEQ ID NO:2, and wherein the KLK1 polypeptide(s) comprises Q145 and/or V188.

In some aspects, a dosage form comprises a pharmaceutically acceptable diluent, adjuvant, or carrier. In some aspects, the dosage form is substantially free of other glycosylated isoforms (glycoforms) of KLK1.

In some aspects, the dosage form has endotoxin levels of less than about 1 EU/mg protein, host cell protein of less than about 100 ng/mg total protein, host cell DNA of less than about 10 pg/mg total protein, and/or is substantially free of aggregates (greater than about 95% appearing as a single peak by SEC HPLC).

In some aspects, the dosage comprises a second agent, for example, an agent selected from one or more of an angiotensin receptor blocker, edavarone, finerenone, and bardoxalone, including combinations thereof. In some embodiments, the angiotensin receptor blocker is selected from one or more of losartan, azilsartan, candesartan, eprosartan, fimasartan, irbesartan, olmesartan, saprisartan, telmisartan, and valsartan, including combinations thereof.

Also included are methods of treating a subject in need thereof, comprising administering to the subject a dosage form as described herein. Some embodiments comprise subcutaneously or intravenously administering the dosage form to the subject. Certain methods relate to treating an ischemic condition in the subject, optionally selected from one or more of brain ischemia (ischemic stroke), transient ischemic attack (TIA), cardiac ischemia (myocardial ischemia), ischemic colitis, limb ischemia, and cutaneous ischemia. Particular methods relate to treating vascular dementia. Some methods relate to treating a hemorrhagic condition in the subject, optionally a hemorrhagic stroke, including intracerebral (within the brain) hemorrhagic stroke and subarachnoid hemorrhagic stroke. some methods relate to treating diabetes, for example, type 2 diabetes (T2D). Certain embodiments relate to treating traumatic brain injury (TBI). Some embodiments relate to treating kidney disease, for example, chronic kidney disease, diabetic kidney disease, or polycystic kidney disease. Also included are methods of treating systemic lupus erythematosus (SLE) and related conditions or complications such as lupus nephritis, pulmonary arterial hypertension (PAH), focal segmental glomerulosclerosis, and essential hypertension.

In some embodiments, subcutaneously administering the dosage forms achieves in the subject a therapeutically-effective serum level of the one or more KLK1 polypeptides, and in some instances maintains in the subject a therapeutically-effective serum level of the one or more KLK1 polypeptides for about or at least about 2, 4, 6, 8, 10, 12, 24, 23, 48, 60, 72, 84, 96 hours or more, or 1, 2, 3, 4, 5, 6, 7, 8, 9, 10, 11, 12, 13, or 14 days or more, following the subcutaneous administration. In some embodiments, intravenously administering the dosage form to the subject achieves in the subject a therapeutically-effective serum level of the one or more KLK1 polypeptides, optionally in about or less than about 0.5, 1, 2, 3, or 4 hours following the intravenous administration. In some embodiments, the therapeutically-effective serum level is about 1.0 to about 5.0 ng/ml, or about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 mg/ml, including all ranges in between, for example, 1.0 to about 5.0 ng/ml, or about 1.0 to about 4.0 ng/ml, or about 1.0 to about 3.0 ng/ml, or about 1.0 to about 2.0 ng/ml, or about 2.0 to about 5.0 ng/ml g, or about 2.0 to about 4.0 ng/ml, or about 2.0 to about 3.0 ng/ml, or about 3.0 to about 5.0 ng/ml, or about 3.0 to about 4.0 ng/ml.

In some embodiments, administration of the dosage form achieves an improved pharmacokinetic profile or biological effect relative to a higher dosage form, for example, a higher dosage form having a total KLK1 polypeptide dosage of at least about 15 µg/kg, or at least about 20 µg/kg, or at least about 50 µg/kg, or at least about 100 µg/kg, or at least about 400 µg/kg or more. In some embodiments, the improved pharmacokinetic profile includes increased serum half-life following a single subcutaneous administration, for example, which is measured at about or at least about 2, 4, 6, 8, 10, 12, 24, 23, 48, 60, 72, 84, 96 hours or more, or 1, 2, 3, 4, 5, 6, 7, 8, 9, 10, 11, 12, 13, or 14 days or more, following the subcutaneous administration.

Certain embodiments comprise administering the dosage form to the subject as a dosing regimen of about once or twice a day, once or twice every two days, once or twice every three days, once or twice every four days, once or twice every five days, once or twice every six days, once or twice every week. Specific embodiments include administering the dosage form to the subject as a dosing regimen of about once a day every three days, for instance, by subcutaneous administration.

Certain embodiments comprise intravenously administering one intravenous dosage form to the subject, followed by subcutaneously administering one or more subcutaneous dosages form to the subject, for example, as a dosing regimen of about once or twice a day, once or twice every two days, once or twice every three days, once or twice every four days, once or twice every five days, once or twice every six days, once or twice every week. In some embodiments, the intravenous administration achieves in the subject a therapeutically-effective serum level of the one or more KLK1 polypeptides in about or less than about 0.5, 1, 2, 3, or 4 hours following the intravenous administration, and the subcutaneous administration maintains the therapeutically-effective serum level for about or at least about 2, 4, 6, 8, 10, 12, 24, 23, 48, 60, 72, 84, 96 hours or more, or 1, 2, 3, 4, 5, 6, 7, 8, 9, 10, 11, 12, 13, or 14 days or more, following the subcutaneous administration.

Certain methods comprise comprising administering a second agent selected from one or more of an angiotensin receptor blocker, edavarone, finerenone, and bardoxalone, including combinations thereof, for example, as part of the same dosage form or as part of a different dosage form or composition. In some embodiments, the angiotensin receptor blocker is selected from one or more of losartan, azilsartan, candesartan, eprosartan, fimasartan, irbesartan, olmesartan, saprisartan, telmisartan, and valsartan, including combinations thereof.

Also included are devices comprising a dosage form as described herein, and which are adapted for or suitable for subcutaneous administration. In some aspects, the device is a syringe. In some aspects, the syringe includes a hypodermic needle assembly attached to the syringe. In some aspects, the syringe includes a protective cover around the needle assembly. In some aspects, the syringe has a needle that is about ½ inch to about ⅝ of an inch in length and has a gauge of about 25 to about 31.

BRIEF DESCRIPTION OF THE DRAWINGS

FIG. 1 shows the results of a KLK1 (DM199) Phase I/II pilot study in humans for the treatment of Type 2 Diabetes (T2D). Patients (n=37) received placebo or one of two doses (high dose of 15 µg/kg, or low dose of 3 µg/kg) of KLK1 every three days for 28 days, and fasting blood glucose (FBG) levels were measured. The high dose (15 µg/kg) showed no significant effect, but the low dose (3 µg/kg) showed a statistically significant (p<0.05) effect on FBG levels relative to baseline. Thus, the lower 3 µg/kg provides an unexpected improvement relative to the higher 15 µg/kg dose.

FIG. 4A provides a summary, FIGS. 4B and 4D show the results for placebo groups, and FIG. 4C shows the results of the (KLK1) DM199 groups. The numbers are a derived measure of insulin resistance (HOMA2-IR) where higher numbers represent greater insulin resistance and denote greater illness.

DETAILED DESCRIPTION

Definitions

Figure 2A:
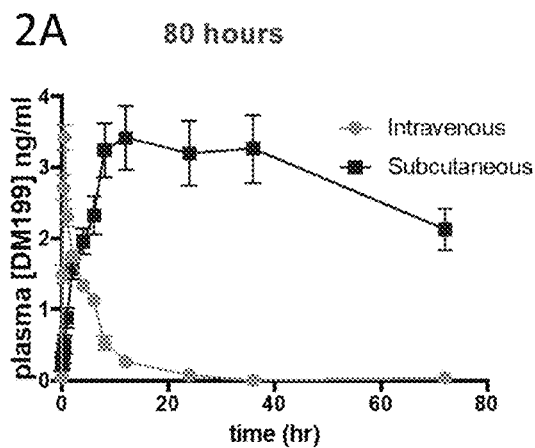
FIGS. 2A-2B show that subcutaneous administration of low-dosage (3 µg/kg; n=12) formulations of mature human KLK1 glycoforms results in significantly prolonged serum half-file, even relative to intravenous administration of low-dosage formulations (0.75 µg/kg; n=12), in healthy human subjects.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

As used herein, the term "amino acid" is intended to mean both naturally occurring and non-naturally occurring amino acids as well as amino acid analogs and mimetics. Naturally-occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

The terms "endotoxin free" or "substantially endotoxin free" relate generally to dosage forms, compositions, solvents, devices, and/or vessels that contain at most trace amounts (e.g., amounts having no clinically adverse physiological effects to a subject) of endotoxin, and preferably undetectable amounts of endotoxin. Endotoxins are toxins associated with certain bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production, it is often desirable to remove most or all traces of endotoxin from drug products and/or drug containers, because even small amounts may cause adverse effects in humans. A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art. Also included are methods of producing KLK1 polypeptides in and isolating them from eukaryotic cells such as mammalian cells to reduce, if not eliminate, the risk of endotoxins being present in a composition of the invention. Preferred are methods of producing KLK1 polypeptides in and isolating them from recombinant cells grown in chemically defined, serum free media.

Endotoxins can be detected using routine techniques known in the art. For example, the Limulus Ameobocyte Lysate assay, which utilizes blood from the horseshoe crab, is a very sensitive assay for detecting presence of endotoxin. In this test, very low levels of LPS can cause detectable coagulation of the limulus lysate due a powerful enzymatic cascade that amplifies this reaction. Endotoxins can also be quantitated by enzyme-linked immunosorbent assay (ELISA). To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/ml, or EU/mg protein. Typically, 1 ng lipopolysaccharide (LPS) corresponds to about 1-10 EU.

The "half-life" of an agent such as KLK1 polypeptide of dosage form can refer to the time it takes for the agent to lose half of its pharmacologic, physiologic, or other activity, relative to such activity at the time of administration into the serum or tissue of an organism, or relative to any other defined time-point. "Half-life" can also refer to the time it takes for the levels of agent to be reduced by half of a starting amount administered into the serum or tissue of an organism, relative to such amount or concentration at the time of administration into the serum or tissue of an organism, or relative to any other defined time-point. The half-life can be measured in serum and/or any one or more selected tissues.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount or level produced by a control composition, sample or test subject. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease in the amount or level produced a control composition, sample or test subject. As one non-limiting example, the comparison can be between the amount or level of a pharmacokinetic parameter/profile or biological/therapeutic response produced by administration of a lower-dosage form (e.g., 1-10 µg/kg) of KLK1 relative to administration of a higher dosage form of KLK1. Other examples of comparisons and "statistically significant" amounts are described herein.

The terms "polypeptide," "protein" and "peptide" are used interchangeably and mean a polymer of amino acids not limited to any particular length. The term "enzyme" includes polypeptide or protein catalysts. The terms include modifications such as myristoylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. In certain embodiments, the polypeptide is a "recombinant" polypeptide, produced by recombinant cell that comprises one or more recombinant DNA molecules, which are typically made of heterologous polynucleotide sequences or combinations of polynucleotide sequences that would not otherwise be found in the cell.

The term "reference sequence" refers generally to a nucleic acid coding sequence, or amino acid sequence, to which another sequence is being compared. All polypeptide and polynucleotide sequences described herein are included as references sequences, including those described by name and those described in the Tables and the Sequence Listing.

A result is typically referred to as "statistically significant" if it is unlikely to have occurred by chance. The significance level of a test or result relates traditionally to the amount of evidence required to accept that an event is unlikely to have arisen by chance. In certain cases, statistical significance may be defined as the probability of making a decision to reject the null hypothesis when the null hypothesis is actually true (a decision known as a Type I error, or "false positive determination"). This decision is often made using the p-value: if the p-value is less than the significance level, then the null hypothesis is rejected. The smaller the p-value, the more significant the result. Bayes factors may also be utilized to determine statistical significance (see Goodman, *Ann Intern Med.* 130:1005-13, 1999).

The term "solubility" refers to the property of a KLK1 polypeptide provided herein to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 6.0, pH 7.0, pH 7.4, pH 8.0 or pH 9.0. In certain embodiments, solubility is measured in water or a physiological buffer such as PBS or NaCl (with or without NaP). In specific embodiments, solubility is measured at relatively lower pH (for example, pH 6.0) and relatively higher salt (for example, 500 mM NaCl and 10 mM NaP). In certain embodiments, solubility is measured in a biological fluid (solvent) such as blood or serum. In certain embodiments, the temperature can be about room temperature (for example, about 20, about 21, about 22, about 23, about 24, or about 25° C.) or about body temperature (37° C.). In certain embodiments, a KLK1 polypeptide has a solubility of at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 25, at least about 30, at least about 35, at least about 40, at least about 45, at least about 50, or at least about 60 mg/ml at room temperature or at 37° C.

"Substantially" or "essentially" means nearly totally or completely, for instance, 95%, 96%, 97%, 98%, 99% or greater of some given quantity.

"Treatment" or "treating," as used herein, includes any desirable effect on the symptoms or pathology of a disease or condition, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

As used herein, the terms "therapeutically effective amount", "therapeutic dose," "prophylactically effective amount," or "diagnostically effective amount" is the amount of an agent (e.g., KLK1 polypeptide or dosage form thereof) needed to elicit the desired biological response following administration.

A "subject," as used herein, includes any animal that exhibits a symptom, or is at risk for exhibiting a symptom, which can be treated with a KLK1 polypeptide or a dosage form thereof. Suitable subjects (patients) include laboratory animals (such as mouse, rat, rabbit, or guinea pig), farm animals, and domestic animals or pets (such as a cat or dog). Non-human primates and, preferably, human patients, are included.

By "isolated" is meant material that is substantially or essentially free from components that normally accompany it in its native state. For example, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances such as host cell proteins or nucleic acids.

A "wild type" or "reference" sequence or the sequence of a "wild type" or "reference" protein/polypeptide may be the reference sequence from which variant polypeptides are derived through the introduction of changes. In general, the "wild type" amino acid sequence for a given protein is the sequence that is most common in nature. Similarly, a "wild type" gene sequence is the polynucleotide sequence for that gene which is most commonly found in nature. Mutations can be introduced into a "wild type" gene (and thus the protein it encodes) either through natural processes or through human induced means.

Each embodiment in this specification is to be applied to every other embodiment unless expressly stated otherwise.

Dosage Forms

Embodiments of the present disclosure relate to dosage forms of one or more tissue kallikrein (KLK1) polypeptides, which are formulated at a total KLK1 polypeptide dosage of about 0.1 µg/kg to about 5 µg/kg or to about 10.0 µg/kg. In some instances, the dosage forms are suitable for (or adapted for) subcutaneous or intravenous administration to a subject, for example, a human subject.

Certain dosage forms comprise, consist, consist essentially of, or are composed of a total KLK1 polypeptide dosage of about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10 µg/kg, including all ranges in between.

For instance, certain dosage forms comprise, consist, consist essentially of, or are composed of a total KLK1 polypeptide dosage of about 0.1 µg/kg to about 10.0 µg/kg, about 0.1 µg/kg to about 9.0 µg/kg, about 0.1 µg/kg to about 8.0 µg/kg, about 0.1 µg/kg to about 7.0 µg/kg, about 0.1 µg/kg to about 6.0 µg/kg, about 0.1 µg/kg to about 5.0 µg/kg, or about 0.1 µg/kg to about 4.0 µg/kg, or about 0.1 µg/kg to about 3.0 µg/kg, or about 0.1 µg/kg to about 2.0 µg/kg, or about 0.01 µg/kg to about 1.0 µg/kg, or about 0.5 µg/kg to about 10.0 µg/kg, about 0.5 µg/kg to about 9.0 µg/kg, about 0.5 µg/kg to about 8.0 µg/kg, about 0.5 µg/kg to about 7.0 µg/kg, about 0.5 µg/kg to about 6.0 µg/kg, about 0.5 µg/kg to about 5.0 µg/kg, or about 0.5 µg/kg to about 4.0 µg/kg, or about 0.5 µg/kg to about 3.0 µg/kg, or about 0.5 µg/kg to about 2.0 µg/kg, or about 0.5 µg/kg to about 1.0 µg/kg, or about 1.0 µg/kg to about 10.0 µg/kg, about 1.0 µg/kg to about 9.0 µg/kg, about 1.0 µg/kg to about 8.0 µg/kg, about 1.0 µg/kg to about 7.0 µg/kg, about 1.0 µg/kg to about 6.0 µg/kg, about 1.0 µg/kg to about 5.0 µg/kg, or about 1.0 µg/kg to about 4.0 µg/kg, or about 1.0 µg/kg to about 3.0 µg/kg, or about 1.0 µg/kg to about 2.0 µg/kg, or about 2.0 µg/kg to about 10.0 µg/kg, or about 2.0 µg/kg to about 9.0 µg/kg, or about 2.0 µg/kg to about 8.0 µg/kg, or about 2.0 µg/kg to about 7.0 µg/kg, or about 2.0 µg/kg to about 6.0 µg/kg, or about 2.0 µg/kg to about 5.0 µg/kg, or about 2.0 µg/kg to about 4.0 µg/kg, or about 2.0 µg/kg to about 3.0 µg/kg, or about 3.0 µg/kg to about 10.0 µg/kg, or about 3.0 µg/kg to about 9.0 µg/kg, or about 3.0 µg/kg to about 8.0 µg/kg, or about 3.0 µg/kg to about 7.0 µg/kg, or about 3.0 µg/kg to about 6.0 µg/kg, or about 3.0 µg/kg to about 5.0 µg/kg, or about 3.0 µg/kg to about 4.0 µg/kg, or about 4.0 µg/kg to about 10.0 µg/kg, or about 4.0 µg/kg to about 9.0 µg/kg, or about 4.0 µg/kg to about 8.0 µg/kg, or about 4.0 µg/kg to about 7.0 µg/kg, or about 4.0 µg/kg to about 6.0 µg/kg, or about 4.0 µg/kg to about 5.0 µg/kg, or about 5.0 µg/kg to about 10.0 µg/kg, or about 5.0 µg/kg to about 9.0 µg/kg, or about 5.0 µg/kg to about 8.0 µg/kg, or about 5.0 µg/kg to about 7.0 µg/kg, or about 5.0 µg/kg to about 6.0 µg/kg, or about 6.0 µg/kg to about 10.0 µg/kg, or about 6.0 µg/kg to about 9.0 µg/kg, or about 6.0 µg/kg to about 8.0 µg/kg, or about 6.0 µg/kg to about 7.0 µg/kg, or about 7.0 µg/kg to about 10.0 µg/kg, or about 7.0 µg/kg to about 9.0 µg/kg, or about 7.0 µg/kg to about 8.0 µg/kg, or about 8.0 µg/kg to about 10.0 µg/kg, or about 8.0 µg/kg to about 9.0 µg/kg, or about 9.0 µg/kg to about 10.0 µg/kg. Specific dosage forms have a total KLK polypeptide dosage of about 2.5 µg/kg to about 3.5 µg/kg, or about 3 µg/kg, including dosage forms suitable for subcutaneous administration. Particular dosage forms have a total KLK polypeptide dosage of about 0.5 µg/kg to about 1.0 µg/kg, or about 0.75 µg/kg, including dosage forms suitable for intravenous administration.

Tissue Kallikrein-1 (KLK1) Polypeptides. As noted above, certain dosage forms comprise one or more tissue kallikrein-1 or KLK1 polypeptides. Tissue kallikreins are members of a gene super family of serine proteases comprising at least 15 separate and distinct proteins (named tissue kallikrein 1 through 15) (Yousef et al., 2001, Endocrine Rev; 22:184-204). Tissue kallikrein-1 is a trypsin-like serine protease. In humans and animal tissues, tissue kallikrein-1 cleaves kininogen into lysyl-bradykinin (also known as kallidin), a decapeptide kinin having physiologic effects similar to those of bradykinin. Bradykinin is a peptide that causes blood vessels to dilate and therefore causes blood pressure to lower. Kallidin is identical to bradykinin with an additional lysine residue added at the N-terminal end and signals through the bradykinin receptor.

The KLK1 gene encodes a single pre-pro-enzyme that is 262 amino acid residues in length and that includes the "pre-" sequence (residues 1-18) and the "pro-" sequence (residues 19-24), which is activated by trypsin-like enzymes. The "mature" and "active" form human KLK1 is a glycoprotein of about 238 amino acid residues (residues 25-262) with a molecular weight of 26 kDa and a theoretical pI of 4.6. KLK1 has five disulfide bonds in its tertiary structure that are believed to be responsible for the protein's high stability, both against trypsin digestion and heat inactivation.

The amino acid sequence of tissue kallikrein-1 is available for a wide variety of species, including, but not limited to, human (SEQ ID NO:1 and SWQ ID NO:2), mouse (see, for example, GenBank: AAA39349.1, Feb. 1, 1994); domestic cat (see, for example, NCBI Reference Sequence: XP_003997527.1, Nov. 6, 2012); gorilla (see, for example, NCBI Reference Sequence: XP_004061305.1, Dec. 3, 2012); cattle (see, for example, GenBank: AAI51559.1, Aug. 2, 2007); dog (see, for example, CBI Reference Sequence: NP_001003262.1, Feb. 22, 2013); rat (see, for example, GenBank: CAE51906.1, Apr. 25, 2006); and olive baboon (see, for example, NCBI Reference Sequence: XP_003916022.1, Sep. 4, 2012). KLK1 is functionally conserved across species in its capacity to release the vasoactive peptide, Lys-bradykinin, from low molecular weight kininogen. A tissue kallikrein-1 polypeptide of the present invention may have any of the known amino acid sequences for KLK1, or a fragment or variant thereof.

In certain embodiments, the KLK1 polypeptide is a "mature" KLK1 polypeptide. In certain embodiments, the KLK1 polypeptide is a human KLK1 polypeptide, optionally a mature human KLK1 polypeptide. In particular embodiments, the KLK1 polypeptide is a recombinant human polypeptide, for example, a recombinant human KLK1 polypeptide, optionally in the mature form. Recombinant human KLK1 (rhKLK1) can provide certain advantages over other sources of KLK1, such as urinary KLK1 (e.g., human KLK1 isolated from human urine), including a homogenous preparation of rhKLK1, simpler regulatory path to licensure, and options to alter the amino acid sequence or glycosylation pattern based on cell culture conditions.

Exemplary amino acid sequences of human tissue kallikrein-1 (hKLK1) polypeptides are provided in Table K1 below.

TABLE K1

Exemplary KLK1 Sequences

| Source | Sequence | SEQ ID NO: |
|---|---|---|
| Human KLK1 | MWFLVLCLALSLGGTGAAPPIQSRIVGGWECEQHSQPWQAALYHFSTFQCGGILVH RQWVLTAAHCISDNYQLWLGRHNLFDDENTAQFVHVSESEPHPGFNMSLLENHTRQ ADEDYSHDLMLLRLTEPADTITDAVKVVELPTEEPEVGSTCLASGWGSIEPENFSF PDDLQCVDLKILPNDECKKAHVQKVTDFMLCVGHLEGGKDTCVGDSGGPLMCDGVL QGVTSWGYVPCGTPNKPSVAVRVLSYVKWIEDTIAENS | 1 |
| Human KLK1 variant | MWFLVLCLALSLGGTGAAPPIQSRIVGGWECEQHSQPWQAALYHFSTFQCGGILVH RQWVLTAAHCISDNYQLWLGRHNLFDDENTAQFVHVSESEPHPGFNMSLLENHTRQ ADEDYSHDLMLLRLTEPADTITDAVKVVELPTQEPEVGSTCLASGWGSIEPENFSF PDDLQCVDLKILPNDECKKVHVQKVTDFMLCVGHLEGGKDTCVGDSGGPLMCDGVL QGVTSWGYVPCGTPNKPSVAVRVLSYVKWIEDTIAENS | 2 |
| Human mature KLK1 | IVGGWECEQHSQPWQAALYHFSTFQCGGILVHRQWVLTAAHCISDNYQLWLGRHNL FDDENTAQFVHVSESFPHPGFNMSLLENHTRQADEDYSHDLMLLRLTEPADTITDA VKVVELPTEEPEVGSTCLASGWGSIEPENFSFPDDLQCVDLKILPNDECKKAHVQK VTDFMLCVGHLEGGKDTCVGDSGGPLMCDGVLQGVTSWGYVPCGTPNKPSVAVRVL SYVKWIEDTIAENS | 3 |
| Human mature KLK1 variant | IVGGWECEQHSQPWQAALYHFSTFQCGGILVHRQWVLTAAHCISDNYQLWLGRHNL FDDENTAQFVHVSESFPHPGFNMSLLENHTRQADEDYSHDLMLLRLTEPADTITDA VKVVELPTQEPEVGSTCLASGWGSIEPENFSFPDDLQCVDLKILPNDECKKVHVQK VTDFMLCVGHLEGGKDTCVGDSGGPLMCDGVLQGVTSWGYVPCGTPNKPSVAVRVL SYVKWIEDTIAENS | 4 |

In certain embodiments, a KLK1 polypeptide comprises, consists, or consists essentially of SEQ ID NO:1-3 or 4, or residues 1-262, residues 19-262, or residues 25-262 of SEQ ID NO:1 or SEQ ID NO:2, including fragments and variants thereof. Amino acids 1 to 18 of SEQ ID NO: 1 and 2 represent the signal peptide, amino acids 19 to 24 represent propeptide sequences, and amino acids 25 to 262 represent the mature peptide. Thus, the preproprotein includes a presumptive 17-amino acid signal peptide, a 7-amino acid proenzyme fragment and a 238-amino acid mature KLK1 protein.

A comparison between SEQ ID NO:1 and SEQ ID NO:2 (or SEQ ID NO:3 and SEQ ID NO:4) shows two amino acid differences between the two hKLK1 amino acid sequences. Single-nucleotide polymorphism (SNPs) between the two individuals within a species account for an E to Q substitution at amino acid residue 145 of 262 and an A to V substitution at position 188 of 262. SEQ ID NO:1 has an E (glutamic acid) at position 145 and an A (alanine) at position 188, while SEQ ID NO:2 has a Q (glutamine) at position 145 and a V (valine) at position 188. In some embodiments, KLK1 polypeptide has an E at position 145; a Q at position 145; an A at position 188; an A at position 188; an E at position 145 and an A at position 188; a Q at position 145 and a V at position 188; a Q at position 145 and an A at position 188; or an E at position 145 and a V at position 188.

As noted above, certain embodiments include active variants and fragments of reference KLK1 polypeptide. A "variant" of a starting or reference polypeptide is a polypeptide that has an amino acid sequence different from that of the starting or reference polypeptide. Such variants include, for example, deletions from, insertions into, and/or substitutions of residues within the amino acid sequence of the polypeptide of interest. A variant amino acid, in this context, refers to an amino acid different from the amino acid at the corresponding position in a starting or reference polypeptide sequence. Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites.

In some embodiments, a KLK polypeptide has at least about 80%, at least about 85%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% amino acid identity to a reference sequence, such as, for example, an amino acid sequence described herein (for example, SEQ ID NOs: 1-4).

In some aspects, a KLK1 polypeptide has at least about 80%, at least about 85%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% amino acid identity to SEQ ID NO:1 or 3, or to a fragment of SEQ ID NO:1 or 3, such as for example, residues 25-262 or residues 78-141 of SEQ ID NO:1. Such a KLK1 polypeptide may have an E or a Q at amino acid residue 145, and/or an A or a V at position 188.

In some aspects, a KLK1 polypeptide has at least about 80%, at least about 85%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% amino acid identity to SEQ ID NO:2 or 4, or to a fragment of SEQ ID NO:2 or 4, such as for example, residues 25-262 or residues 78-141 of SEQ ID NO:2. Such a KLK1 polypeptide may have an E or a Q at amino acid residue 145, and/or an A or a V at position 188.

"Percent (%) amino acid sequence identity" with respect to a polypeptide is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, or Megalign (DNASTAR) software. Those skilled in the art can determine appropriate parameters for measuring alignment, including any algorithms needed to achieve maximal alignment over the full length of the sequences being compared. The ALIGN-2 program is publicly available through Genentech, Inc., South San Francisco, California.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as: 100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Variants may also include heterologous sequences or chemical modifications which are added to the reference KLK1 polypeptide, for example, to facilitate purification, improve metabolic half-life, or make the polypeptide easier to identify. Examples include affinity tags such as a His-tag, Fc regions, and/or a PEGylation sequence and PEG.

The term "fragment" includes smaller portions of a KLK1 polypeptide (or variants thereof) that retain the activity of a KLK1 polypeptide. Fragments includes, for example, a KLK1 polypeptide fragment that ranges in size from about 20 to about 50, about 20 to about 100, about 20 to about 150, about 20 to about 200, or about 20 to about 250 amino acids in length. In other embodiments, a KLK1 polypeptide fragment ranges in size from about 50 to about 100, about 50 to about 150, about 50 to about 200, or about 50 to about 250 amino acids in length. In other embodiments, a KLK1 polypeptide fragment ranges in size from about 100 to about 150, about 100 to about 200, about 100 to about 250, about 150 to about 175, about 150 to about 200, or about 150 to about 250 amino acids in length. In other illustrative embodiments, a KLK1 polypeptide fragment ranges in size from about 200 to about 250 amino acids in length. Certain embodiments comprise a polypeptide fragment of a full-length KLK1 of about, up to about, or at least about 50, 60, 70, 80, 90, 100, 110, 120, 130, 140, 150, 160, 170, 180, 190, 200, 210, 220, 230, 240, 250 or more (e.g., contiguous) amino acid residues. In some embodiments, a fragment may have residues 25-262 or residues 78-141 of a preproprotein sequence. In some embodiments, a fragment may be any such fragment size, as described above, of SEQ D NO: 1 or SEQ ID NO:2.

In some instances, fragments and variants of a KLK1 polypeptide retain the enzymatic capacity to release the vasoactive peptide, Lys-bradykinin, from low molecular weight kininogen. In some embodiments, an active variant or fragment retains serine protease activity of a KLK1 polypeptide that releases kallidin from a higher molecular weight precursor such as kininogen, or that cleaves a substrate similar to kininogen such as D-val-leu-arg-7 amido-4-trifluoromethylcoumarin to release a colorimetric or fluorometric fragment. The protease activity of KLK1 polypeptides can be measured in an enzyme activity assay by measuring either the cleavage of low-molecular-weight kininogen, or the generation of lys-bradykinin. In one assay format, a labeled substrate is reacted with the KLK1 glycoform, and the release of a labeled fragment is detected. One example of such a fluorogenic substrate suitable for KLK1 measurement of activity is D-val-leu-arg-7 amido-4-trifluoromethylcoumarin (D-VLR-AFC, FW 597.6) (Sigma, Cat #V2888 or Ana Spec Inc Cat #24137). When D-VLR-AFC is hydrolyzed, the free AFC produced in the reaction can be quantified by fluorometric detection (excitation 400 nm, emission 505 nm) or by spectrophotometric detection at 380 nm (extinction coefficient=12,600 at pH 7.2). Other methods and substrates may also be used to measure KLK1 proteolytic activity.

Glycoforms and Mixtures Thereof. In certain embodiments, the dosage form comprises a mixture of one or more KLK1 polypeptide glycoforms, including dosage forms that comprise defined ratios of double and triple glycosylated KLK1 polypeptides (see U.S. application Ser. No. 14/677,122, incorporated by reference in its entirety).

Human kallikrein has three potential Asn-linked (N-linked) glycosylation sites at residues 78, 84, and 141, relative to the mature amino acid sequence shown, for example, in SEQ ID NO: 3 or 4, as well as putative O-linked glycosylation sites. However, O-linked glycosylation is not detected in naturally-occurring KLK1. By SDS-PAGE analysis, KLK1 polypeptides glycosylated at all three positions (positions 78, 84, and 141) are detected as the high molecular weight band and are referred to herein as the high-molecular weight, triple glycosylated glycoform of KLK1 (or "high glycoform" or "triple glycoform" KLK1). By SDS-PAGE analysis, KLK1 polypeptides glycosylated at only two of three available positions (positions 78 and 84) are detected as a low molecular weight band and are referred to herein as the low-molecular weight, double glycosylated glycoform of KLK1 (or as "low glycoform" or "double glycoform" KLK1).

Certain dosage forms therefore comprise a mixture of KLK1 glycoforms at a defined ratio, for example, comprising a first KLK1 polypeptide and a second KLK1 polypeptide, wherein the first KLK1 polypeptide has three glycans attached at the three different positions available for glycosylation in the polypeptide, and wherein the second KLK1 polypeptide has two glycans attached at only two of the three different positions available for glycosylation in the polypeptide. In certain embodiments, the first and second KLK1 polypeptides are present in the dosage form at a ratio of about 45:55 to about 55:45, including, for example, about 46:54, about 47:53, about 48:52, about 49:51, about 51:49, about 52:48, about 53:47, and about 54:46, including all integers and decimal points in between. In specific embodiments, the first and second KLK1 polypeptides are present in the dosage form at a ratio of about 50:50. In some embodiments, the ratio of the first and second KLK1 polypeptides is not about 60:40. In some embodiments, the ratio of the first and second KLK1 polypeptides is not about 40:60. In certain embodiments, the dosage form is free or substantially free of other glycosylated isoforms (glycoforms) of KLK1.

Some dosage forms comprise a triple glycoform of a KLK1 polypeptide and a double glycoform of a KLK1 polypeptide, wherein the triple glycoform and the double glycoform are present in the dosage form at a ratio of about 45:55 to about 55:45 including, for example, about 46:54, about 47:53, about 48:52, about 49:51, about 51:49, about 52:48, about 53:47, and about 54:46. In some embodiments, the triple glycoform and the double glycoform are present in the dosage form at a ratio of about 50:50. In some embodiments, the ratio of the triple glycoform and double glycoform is not about 60:40. In some embodiments, the ratio of the triple glycoform and double glycoform is not about 40:60. In certain embodiments, the dosage form is free or substantially free of other glycosylated isoforms (glycoforms) of KLK1.

The ratios of the double and triple glycosylated isoforms of KLK1 can be detected and quantitated by a variety of methods, including high performance liquid chromatography (HPLC), which may include reversed phase (RP-HPLC), lectin affinity chromatography and lectin affinity electrophoresis. The preparation and characterization of KLK1 glycoform mixtures is described in U.S. application Ser. No. 14/677,122, incorporated by reference in its entirety.

Additional Agents. In certain embodiments, the dosage form comprises one more additional therapeutic agents, for example, a second therapeutic agent. In some embodiments, the additional agent is selected from one or more of an angiotensin receptor blocker, edavarone, finerenone, and bardoxalone, including combinations thereof. Examples of angiotensin receptor blockers include losartan, azilsartan, candesartan, eprosartan, fimasartan, irbesartan, olmesartan, saprisartan, telmisartan, and valsartan, including combinations thereof.

Purity. In some embodiments, the "purity" of a dosage form is characterized, for example, by the amount (e.g., total amount, relative amount, percentage) of host cell protein(s), host cell DNA, endotoxin, and/or percentage single peak purity by SEC HPLC. In some instances, the purity of a dosage form is characterized by the amount (e.g., percentage) of KLK1 polypeptide relative to other components, for example, any one or more of the foregoing.

In some embodiments, purity of a dosage form is characterized relative to or by the levels or amount of host cell proteins. The host cells used for recombinant expression may range from bacteria and yeast to cell lines derived from mammalian or insect species. The cells contain hundreds to thousands of host cell proteins (HCPs) and other biomolecules that could contaminate the final product. The HCP may be secreted along with the protein of interest, or released by accidental lysing of the cells, and may contaminate the protein of interest. Two types of immunological methods may be applied to HCP analysis: Western blotting (WB) and immunoassay (IA), which includes techniques such as ELISA and sandwich immunoassay or similar methods using radioactive, luminescent, or fluorescent reporting labels. Compositions of the present invention may include host cell protein of less than about 500, less than about 400, less than about 300, less than about 200, less than about 100 or less than about 50 ng/mg total protein.

In some instances, purity is characterized relative to or by the levels or amount of host cell DNA. Detection of residual host cell DNA may be performed by Polymerase Chain Reaction (PCR) with a variety of primers for sequences in the host cell genome. Residual host cell DNA is generally reported as being below a certain threshold level, but may also be quantitated with a rPCR method. Compositions of the present invention may include host cell deoxyribonucleic acid (DNA) of less than about 100, less than about 90, less than about 80, less than about 70, less than about 60, less than about 50, less than about 40, less than about 30, less than about 20, or less than about 10 pg/mg total protein.

In certain embodiments, purity is characterized relative to or by the amount or levels of endotoxin. As noted herein, endotoxin is extremely potent, heat stable, passes sterilizing membrane filters, and is present everywhere bacteria are or have been present. An Endotoxin Unit (EU) is a unit of biological activity of the USP Reference Endotoxin Standard.

The bacterial endotoxins test (BET) is a test to detect or quantify endotoxins from Gram-negative bacteria using amoebocyte lysate (white blood cells) from the horseshoe crab (Limulus *polyphemus* or *Tachypleus tridentatus*). Limulus amoebocyte lysate (LAL) reagent, FDA approved, is used for all USP endotoxin tests. There are at least three methods for this test: Method A, the gel-clot technique, which is based on gel formation; Method B, the turbidimetric technique, based on the development of turbidity after cleavage of an endogenous substrate; and Method C, the chromogenic technique, based on the development of color after cleavage of a synthetic peptide-chromogen complex.

At least two types of endotoxin tests are described in the USP <85> BET. Photometric tests require a spectrophotometer, endotoxin-specific software and printout capability. The simplest photometric system is a handheld unit employing a single-use LAL cartridge that contains dried, pre-calibrated reagents; there is no need for liquid reagents or standards. The FDA-approved unit is marketed under the name of Endosafe®-PTS™. The device requires about 15 minutes to analyze small amounts of sample, a 25 μL aliquot from CSP diluted in a sterile tube, and to print out results. In contrast, gel-clot methods require a dry-heat block, calibrated pipettes and thermometer, vortex mixer, freeze-dried LAL reagents, LAL Reagent Water (LRW) for hydrating reagents and depyrogenated glassware. In this clot test, diluted sample and liquid reagents require about an hour for sample and positive-control preparation and an hour's incubation in a heat block; results are recorded manually. Thus, the simplicity and speed of the automated system make it ideally suited to the pharmacy setting.

In some instances, the purity of a dosage form is characterized by the degree of aggregation. For instance, the degree of aggregation of KLK1 can be determined by Size-exclusion chromatography (SEC), which separates particles on the basis of size. It is a generally accepted method for determining the tertiary structure and quaternary structure of purified proteins. SEC is used primarily for the analysis of large molecules such as proteins or polymers. SEC works by trapping these smaller molecules in the pores of a particle. The larger molecules simply pass by the pores as they are too large to enter the pores. Larger molecules therefore flow through the column quicker than smaller molecules, that is, the smaller the molecule, the longer the retention time. Certain compositions are also substantially free of aggregates (greater than about 95% appearing as a single peak by SEC HPLC). Certain embodiments are free of aggregates with greater than about 96%, about 97%, about 98%, or about 99%, appearing as a single peak by SEC HPLC.

In certain embodiments, the "purity" of the KLK1 polypeptide(s) in a dosage form is specifically defined. For instance, certain dosage forms comprise one or more hKLK1 polypeptides that are at least about 80, at least about 85, at least about 90, at least about 91, at least about 92, at least about 93, at least about 94, at least about 95, at least about 96, at least about 97, at least about 98, at least about 99, or 100% pure, including all decimals in between, relative to other components in the dosage form. Purity can be measured, for example and by no means limiting, by high performance liquid chromatography (HPLC), a well-known form of column chromatography used frequently in biochemistry and analytical chemistry to separate, identify, and quantify compounds.

In certain embodiments, the dosage form has one or more of the following determinations of purity: less than about 1 EU endotoxin/mg protein, less that about 100 ng host cell protein/mg protein, less than about 10 pg host cell DNA/mg protein, and/or greater than about 95% single peak purity by SEC HPLC.

In some instances, the dosage forms are formulated with pharmaceutically acceptable excipients, diluents, adjuvants, or carriers, for instance, to optimize stability and achieve isotonicity. In certain aspects, the pH of the dosage form is near physiological pH or about pH 7.4, including about pH 6.5, about 7.0, about 7.1, about 7.2, about 7.3, about 7.4, about 7.5, about 7.6, about 7.7, about 7.8, about 7.9, about 8.0, about 8.5, or any range thereof. In some embodiments, a dosage form comprises a KLK1 polypeptide in combination with a physiologically acceptable carrier. Such carriers include pharmaceutically acceptable carriers, excipients, or stabilizers which are nontoxic to the cell or mammal being exposed thereto at the dosages and concentrations employed. Methods of formulation are well known in the art and are disclosed, for example, in Remington: The Science and Practice of Pharmacy, Mack Publishing Company, Easton, Pa., Edition 21 (2005).

The phrase "physiologically-acceptable" or "pharmaceutically-acceptable" refers to molecular entities and compositions that do not produce a significant allergic or similar untoward reaction when administered to a human. Typically, such compositions are prepared as injectables, either as liquid solutions or suspensions; solid forms suitable for solution in, or suspension in, liquid prior to injection can also be prepared. The preparations can also be emulsified.

As used herein, "carrier" includes any and all solvents, dispersion media, vehicles, coatings, diluents, isotonic and absorption delaying agents, buffers, carrier solutions, suspensions, colloids, and the like. Except insofar as any conventional media or agent is incompatible with the active ingredient, its use in the therapeutic compositions is contemplated.

The dosage forms described herein may be formulated for administered by a variety of techniques, including, for example, subcutaneous and intravenous administration. Particular embodiments include administration by subcutaneous injection. In some instances, a subcutaneous injection (abbreviated as SC, SQ, sub-cu, sub-Q or subcut with SQ) is administered as a bolus into the subcutis, the layer of skin directly below the dermis and epidermis, collectively referred to as the cutis. Exemplary places on the body where people can inject SC most easily include, without limitation, the outer area of the upper arm, just above and below the waist, excepting in certain aspects the area right around the navel (a ~2-inch circle), the upper area of the buttock, just behind the hip bone, and the front of the thigh, midway to the outer side, about 4 inches below the top of the thigh to about 4 inches above the knee. These areas can vary with the size of the person. Also, changing the injection site can prevent lumps or small dents called lipodystrophies from forming in the skin.

Subcutaneous injections usually go into the fatty tissue below the skin and in certain instances can utilize a smaller, shorter needle. In specific instances, a needle that is about ½ inch to about ⅝ of an inch in length with a gauge of about 25 to about 31 is sufficient to subcutaneously administer the medication. As will be appreciated by someone skilled in the art, these are general recommendations and SC injections may be administered with needles of other sizes. In some embodiments SC administration is performed by pinching-up on the tissue to prevent injection into the muscle, and/or insertion of the needle at a ~45° angle to the skin.

Also included are methods of treating a subject in need thereof, comprising administering to the subject an effective amount of a dosage form as described herein. For instance, certain embodiments include methods of treating an ischemic condition, vascular dementia, a hemorrhagic condition, traumatic brain injury (TBI), diabetes, or kidney disease, among others.

Thus, in some embodiments, the subject has an ischemic condition. Non-limiting examples include brain ischemia (ischemic stroke), transient ischemic attack (TIA), cardiac ischemia (myocardial ischemia), ischemic colitis, limb ischemia, and cutaneous ischemia. In some embodiments, the subject has vascular dementia. In some embodiments, the subject has a hemorrhagic condition, for example, a hemorrhagic stroke, including intracerebral (within the brain) hemorrhagic stroke and subarachnoid hemorrhagic stroke. In some embodiments, the subject has diabetes, for example, type 2 diabetes (T2D). In particular embodiments, the subject has a traumatic brain injury (TBI). In some embodiments, the subject has a kidney disease, for example, chronic kidney disease, diabetic kidney disease, or polycystic kidney disease. In some embodiments, the subject has systemic lupus erythematosus (SLE) or a related condition or complication such as lupus nephritis. In particular embodiments, the subject has pulmonary arterial hypertension (PAH), focal segmental glomerulosclerosis, or essential hypertension. These and related medical conditions can be diagnosed according to routine techniques in the art.

In certain instances, administration of the dosage form achieves in the subject a therapeutically-effective serum level of the one or more KLK1 polypeptides. In some instances, administration of the dosage form achieves a therapeutically-effective serum level of the one or more KLK1 polypeptides in about or less than about 0.5, 1, 2, 3, 4, 5, 6, 7, 8, 9, 10, 11, 12, 13, 14, 15, 16, 17, 18, 19, or 20 hours following administration. In some instances, the dosage form is administered intravenously or subcutaneously. In some instances, the therapeutically-effective serum level is about or at least about 1.0 to about or at least about 5.0 ng/ml, or about or at least about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 mg/ml, including all ranges in between.

In some instances, administration of the dosage form achieves and maintains in the subject a therapeutically-effective serum level of the one or more KLK1 polypeptides. For instance, in some embodiments, administration of the dosage forms achieves a therapeutically-effective serum level of the one or more KLK1 polypeptides in about or less than about 0.5, 1, 2, 3, 4, 5, 6, 7, 8, 9, 10, 11, 12, 13, 14, 15, 16, 17, 18, 19, or 20 hours, and maintains in the subject a therapeutically-effective serum level of the one or more KLK1 polypeptides for about or at least about 0.5, 1, 2, 4, 6, 8, 10, 12, 24, 23, 48, 60, 72, 84, 96 hours or more, or 1, 2, 3, 4, 5, 6, 7, 8, 9, 10, 11, 12, 13, or 14 days or more, following the administration (e.g., a single subcutaneous or intravenous administration). In some instances, the therapeutically-effective serum level is about or at least about 1.0 to about or at least about 5.0 ng/ml, or about or at least about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 mg/ml, including all ranges in between.

In some instances, administration of the dosage form achieves or results in an improved pharmacokinetic profile or biological (e.g., therapeutic) effect relative to a higher KLK1 polypeptide dosage form. For example, in some instances, subcutaneous administration of the dosage form achieves an improved pharmacokinetic profile or biological (e.g., therapeutic) effect relative to a dosage form having a total KLK1 polypeptide dosage of at least about 15 µg/kg, at least about 20 µg/kg, or at least about 50 µg/kg, or at least about 100 µg/kg, or at least about 400 µg/kg, or more. In some instances, the improved pharmacokinetic profile includes increased serum half-life following a single subcutaneous or intravenous administration, which is measured, for example, at about or at least about 2, 4, 6, 8, 10, 12, 24, 23, 48, 60, 72, 84, 96 hours or more, or 1, 2, 3, 4, 5, 6, 7, 8, 9, 10, 11, 12, 13, or 14 days or more, following the subcutaneous administration (e.g., a single subcutaneous administration).

Certain embodiments include a dosage regimen of administering one or more KLK1 dosage forms at defined intervals over a period of time. For example, certain dosage regimens include administering a KLK1 dosage form once or twice a day, once or twice every two days (e.g., once a day every other day), once or twice every three days (e.g., once a day every third day following an initial or earlier administration), once or twice every four days, once or twice every five days, once or twice every six days, once or twice every week, once or twice every other week. Specific dosage regimens include administering a KLK1 dosage form once a day every three days (e.g., once a day every third day following an initial or earlier administration), including wherein the dosage form is administered subcutaneously.

Specific embodiments include intravenously administering at least one intravenous dosage form to the subject, followed by subcutaneously administering one or more subcutaneous dosages form to the subject, for example, as a dosing regimen of about once or twice a day, once or twice every two days, once or twice every three days, once or twice every four days, once or twice every five days, once or twice every six days, once or twice every week. In particular embodiments, the intravenous administration or dosage form achieves in the subject a therapeutically-effective serum level of the one or more KLK1 polypeptides in about or less than about 0.5, 1, 2, 3, or 4 hours following the intravenous administration, and the subcutaneous administration or dosage form maintains the therapeutically-effective serum level for about or at least about 2, 4, 6, 8, 10, 12, 24, 23, 48, 60, 72, 84, 96 hours or more, or 1, 2, 3, 4, 5, 6, 7, 8, 9, 10, 11, 12, 13, or 14 days or more, following the subcutaneous administration.

Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA. In some instances, preparation are substantially endotoxin-free or pyrogen-free, as described herein. According to the FDA Guidance for Industry; Estimating the Maximum Safe Starting Dose in Initial Clinical Trial for Therapeutics in Adult Healthy Volunteers (July 2005), Appendix D: Converting animal doses to human equivalent doses. A human equivalent dose is 1/7 the rat dose and a human equivalent dose is 1/12 a mouse dose.

In some embodiments, a dosage form describe herein is administered with one or more additional therapeutic agents or modalities. In some aspects, administration of the dosage form allows for the effectiveness of a lower dosage of other therapeutic modalities when compared to the administration of the other therapeutic modalities alone, providing relief from the toxicity observed with the administration of higher doses of the other modalities. One or more additional therapeutic agents may be administered before, after, and/or coincident (e.g., together with) to the administration of a dosage form described herein. A dosage form and any additional therapeutic agents can be administered separately or as part of the same mixture or cocktail. As used herein, an additional therapeutic agent includes, for example, an agent whose use for the treatment of a condition (e.g., an ischemic or hemorrhagic condition) is known to persons skilled in the art. Examples of additional agents include angiotensin receptor blockers, edavarone, finerenone, and bardoxalone, including combinations thereof. Particular examples of angiotensin receptor blockers include losartan, azilsartan, candesartan, eprosartan, fimasartan, irbesartan, olmesartan, saprisartan, telmisartan, and valsartan, including combinations thereof.

Devices. Also included are devices that comprise a dosage form described herein, including devices suitable for subcutaneous or intravenous delivery. In some embodiments, the device is a syringe. In some embodiments, the syringe is attached to a hypodermic needle assembly, optionally comprising a protective cover around the needle assembly. In some embodiments, the needle may be about ½ inch to about ⅝ of an inch in length and has a gauge of about 25 to about 31. Certain embodiments thus include devices that attached or attachable to a needle assembly that is suitable for subcutaneous administration, comprising a dosage form described herein. For example, certain devices include a vial or syringe, optionally where the vial or syringe is attachable to or is attached to a hypodermic needle assembly. Also included are vials having a rubber cap, where a needle/syringe can be inserted into the vial via the rubber cap to withdraw the dosage form for subcutaneous administration.

In particular aspects, the device is a syringe that is attachable or attached to a hypodermic needle, and is packaged with one or more removable and/or permanent protective covers around the needle or needle assembly. For instance, a first removable protective cover (which is removed during administration) can protect a user or other person from the needle prior to administration, and a second protective cover can be put (i.e., snapped) into place for safe disposal of the device after administration.

The present invention is illustrated by the following examples. It is to be understood that the particular examples, materials, amounts, and procedures are to be interpreted broadly in accordance with the scope and spirit of the invention as set forth herein.

EXAMPLES

Example 1

Pharmacokinetics of Low-Dosage KLK1 Formulations in Humans

The pharmacokinetics of low-dosage KLK1 formulations were evaluate in humans. The formulations are composed of mixture of double and triple glycosylation isoforms of mature human KLK1, which were prepared as described in U.S. application Ser. No. 14/677,122 (incorporated by reference).

A single dose comparison study was designed to establish safety, tolerability and pharmacokinetics of the KLK1 formulation after 30 minute IV infusion and a single subcutaneous injection. The IV dose was 0.75 µg/kg and the subcutaneous dose was 3 µg/kg. Study groups consisted of 12 volunteers with 6 women and 6 men in each.

The intravenous dose was supplied to the clinical site as a 104.4 mg/ml drug product dissolved in phosphate-buffered saline (pH=7.2). The volume of KLK1 polypeptide required for dosing was calculated based on the body weight of each study volunteer and the dose level. The subcutaneous dose was provided as a 26.1 mg/ml solution in phosphate-buffered saline. Prior to administration this dosage was diluted to 2.61 mg/ml in normal saline and the volume of injection adjusted according to the body weight of the study participant.

The concentration of KLK1 in plasma was measured by ELISA using a KLK1-specific antibody. This method has been developed and validated for use in human clinical trials.

Figure 2B:
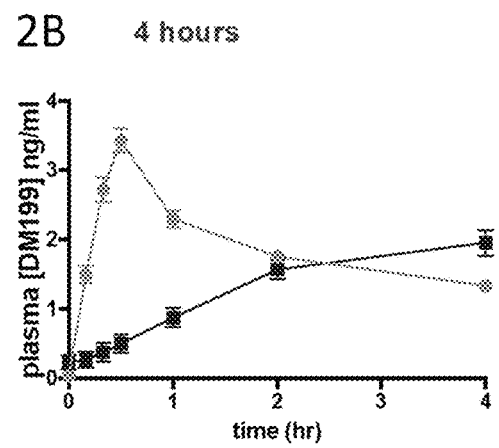

As shown in FIGS. 2A-2B, subcutaneous administration of low-dosage (3 µg/kg; n=12) formulations of mature human KLK1 glycoforms not only achieved effective plasma levels of KLK1, but also resulted in significantly prolonged serum half-file, even relative to intravenous administration of low-dosage formulations (0.75 µg/kg; n=12), in healthy human subjects. Intravenous administration of low-dosage formulations of mature human KLK1 glycoforms rapidly achieved effective plasma levels of KLK1. FIG. 2A shows the serum levels at 80 hours and FIG. 2B shows serum levels at 4 hours post-administration.

Figure 3:
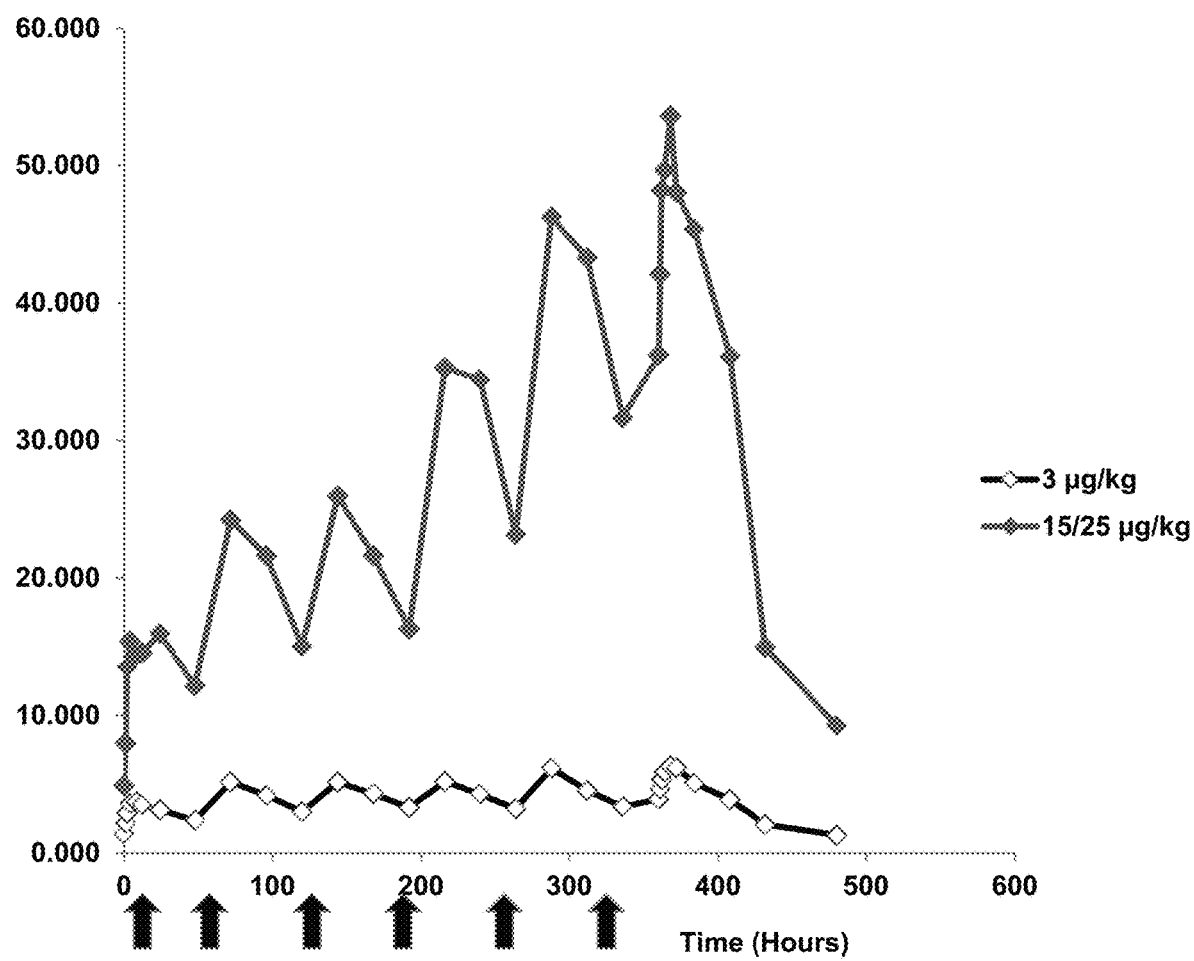
FIG. 3 shows the results of a clinical study in which 3 µg/kg dosage of KLK1 (DM199) maintained fairly steady drug levels at the desired or therapeutically-effective serum/plasma concentration of about 3-5 ng/ml. In contrast, the higher 15/25 µg/kg dosage caused plasma levels to be proportionally higher with greater fluctuation between doses.

The pharmacokinetic (PK) profile of two KLK1 subcutaneous dosing strategies (3 µg/kg; and 15/25 µg/kg) in healthy volunteers was also evaluated in an phase I clinical study. The results are shown in FIG. 3. The points represent the mean values derived from six participants per group. The arrows represent times of dosing. The 3 µg/kg dose, which is considered the target dose from the most recent patent, maintained fairly steady drug levels at the desired or therapeutically-effective serum/plasma concentration of about 3-5 ng/ml. In contrast, the higher dosage caused levels to be proportionally higher with a greater fluctuation between doses.

Figures 4A, 4B, 4C, 4D:
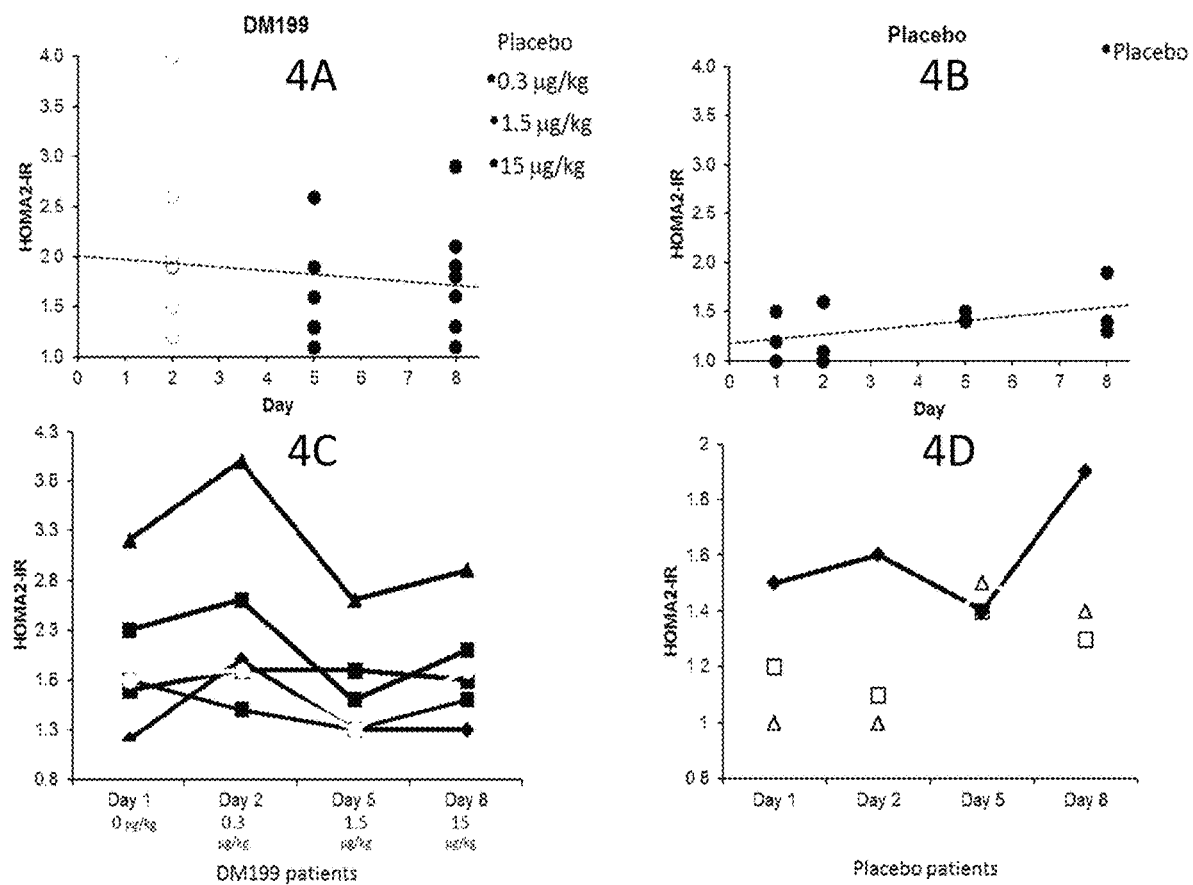
FIGS. 4A-4D shows the results of a KLK1 dosage test performed in patients with Type 2 diabetes.

A dosage test of KLK1 was performed in patients with Type 2 diabetes. The results are shown in FIGS. 4A-4D. The points are results of a meal tolerance test conducted ~2 hours after dosing, using the HOMA2-IR measure of insulin resistance three hours after dosing. The numbers are a derived measure of insulin resistance where higher numbers represent greater insulin resistance and denote greater illness. FIG. 4D shows the results from the placebo group and the FIG. 4C shows the results of the drug groups (DM199). The Day 1 test was run as a baseline followed by single doses of the indicated dose level on subsequent days. The insulin resistance improved on Day 5 when a low dose was tested compared to the results of Day 8 when a higher dose was tested (FIG. 4C), suggesting that the low dosage was more effective.

Figures 5A, 5B:
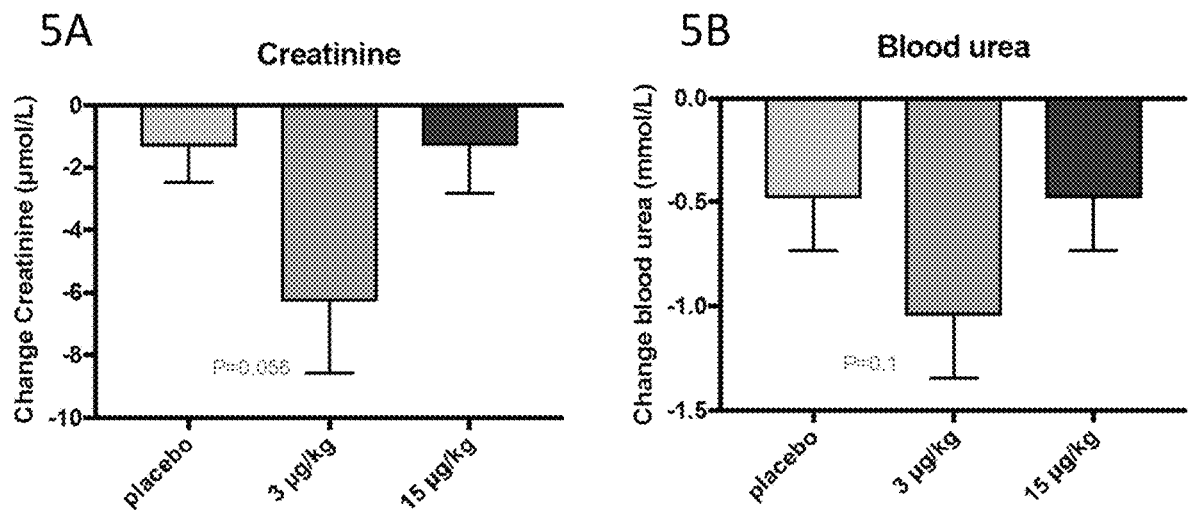
FIGS. 5A-5B show the results of a 28-day multiple dose study in Type 2 Diabetic patients (n=12-13 per group) on measurements of kidney function (creatinine, blood urea). The low dosage (3 µg/kg) had a significantly greater effect than the higher dosage (15 µg/kg) on improving measurements of kidney function.

A 28-day multiple dose study in Type 2 Diabetic patients (n=12-13 per group) was also performed. The results are shown in FIGS. 5A-5B. The bars represent the mean±SEM change from baseline serum creatinine and urea concentration. These are typical measures of kidney function where above normal values indicate kidney impairment. This result indicates that the low dose (3 μg/kg) had a significantly greater effect than the higher dose on improving measurements of kidney function. The P values are based on comparisons between the 3 μg/kg group and placebo.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

The invention claimed is:

1. A method of treating vascular dementia in a subject in need thereof, comprising subcutaneously or intravenously administering to the subject a dosage form comprising:
   a first tissue kallikrein (KLK1) polypeptide and a second KLK1 polypeptide which are formulated at a total KLK1 polypeptide dosage of 0.5 μg/kg to 5.0 μg/kg, wherein the first KLK1 polypeptide has three N-linked glycans attached at residues 78, 84, and 141 as defined by SEQ ID NO: 3 or 4, and the second KLK1 polypeptide has two N-linked glycans attached at residues 78 and 84 but not 141 as defined by SEQ ID NO: 3 or 4; and
   wherein the first KLK1 polypeptide and the second KLK1 polypeptides are present in the dosage form at a ratio of about 45:55 to about 55:45.

2. The method of claim 1, comprising subcutaneously administering the dosage form to the subject, wherein subcutaneous administration of the dosage forms achieves in the subject a therapeutically-effective serum level of the KLK1 polypeptides and maintains the therapeutically-effective serum level for about or at least about 2, 4, 6, 8, 10, 12, 24, 23, 48, 60, 72, 84, 96 hours or more, or 1, 2, 3, 4, 5, 6, 7, 8, 9, 10, 11, 12, 13, or 14 days or more, following the subcutaneous administration.

---

SEQUENCE LISTING

```
Sequence total quantity: 4
SEQ ID NO: 1             moltype = AA  length = 262
FEATURE                  Location/Qualifiers
source                   1..262
                         mol_type = protein
                         organism = Homo sapiens
SEQUENCE: 1
MWFLVLCLAL SLGGTGAAPP IQSRIVGGWE CEQHSQPWQA ALYHFSTFQC GGILVHRQWV   60
LTAAHCISDN YQLWLGRHNL FDDENTAQFV HVSESFPHPG FNMSLLENHT RQADEDYSHD  120
LMLLRLTEPA DTITDAVKVV ELPTEEPEVG STCLASGWGS IEPENFSFPD DLQCVDLKIL  180
PNDECKKAHV QKVTDFMLCV GHLEGGKDTC VGDSGGPLMC DGVLQGVTSW GYVPCGTPNK  240
PSVAVRVLSY VKWIEDTIAE NS                                          262

SEQ ID NO: 2             moltype = AA  length = 262
FEATURE                  Location/Qualifiers
source                   1..262
                         mol_type = protein
                         organism = Homo sapiens
SEQUENCE: 2
MWFLVLCLAL SLGGTGAAPP IQSRIVGGWE CEQHSQPWQA ALYHFSTFQC GGILVHRQWV   60
LTAAHCISDN YQLWLGRHNL FDDENTAQFV HVSESFPHPG FNMSLLENHT RQADEDYSHD  120
LMLLRLTEPA DTITDAVKVV ELPTQEPEVG STCLASGWGS IEPENFSFPD DLQCVDLKIL  180
PNDECKKVHV QKVTDFMLCV GHLEGGKDTC VGDSGGPLMC DGVLQGVTSW GYVPCGTPNK  240
PSVAVRVLSY VKWIEDTIAE NS                                          262

SEQ ID NO: 3             moltype = AA  length = 238
FEATURE                  Location/Qualifiers
source                   1..238
                         mol_type = protein
                         organism = Homo sapiens
SEQUENCE: 3
IVGGWECEQH SQPWQAALYH FSTFQCGGIL VHRQWVLTAA HCISDNYQLW LGRHNLFDDE   60
NTAQFVHVSE SFPHPGFNMS LLENHTRQAD EDYSHDLMLL RLTEPADTIT DAVKVVELPT  120
EEPEVGSTCL ASGWGSIEPE NFSFPDDLQC VDLKILPNDE CKKAHVQKVT DFMLCVGHLE  180
GGKDTCVGDS GGPLMCDGVL QGVTSWGYVP CGTPNKPSVA VRVLSYVKWI EDTIAENS    238

SEQ ID NO: 4             moltype = AA  length = 238
FEATURE                  Location/Qualifiers
source                   1..238
                         mol_type = protein
                         organism = Homo sapiens
SEQUENCE: 4
IVGGWECEQH SQPWQAALYH FSTFQCGGIL VHRQWVLTAA HCISDNYQLW LGRHNLFDDE   60
NTAQFVHVSE SFPHPGFNMS LLENHTRQAD EDYSHDLMLL RLTEPADTIT DAVKVVELPT  120
QEPEVGSTCL ASGWGSIEPE NFSFPDDLQC VDLKILPNDE CKKVHVQKVT DFMLCVGHLE  180
GGKDTCVGDS GGPLMCDGVL QGVTSWGYVP CGTPNKPSVA VRVLSYVKWI EDTIAENS    238
```

3. The method of claim 1, comprising intravenously administering the dosage form to the subject, wherein intravenous administration of the dosage forms achieves in the subject a therapeutically-effective serum level of the KLK1 polypeptides in about or less than about 0.5, 1, 2, 3, or 4 hours following the intravenous administration.

4. The method of claim 2 or 3, where the therapeutically-effective serum level is about 1.0 to about 5.0 ng/ml.

5. The method of claim 1, wherein administration of the dosage form achieves an improved pharmacokinetic profile or biological effect relative to a higher dosage form having a total KLK1 polypeptide dosage of at least about 15 µg/kg.

6. The method of claim 1, wherein the dosage form comprises a total KLK1 polypeptide dosage of about 0.7, 0.75, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 µg/kg.

7. The method of claim 1, wherein the dosage form comprises a total KLK1 polypeptide subcutaneous dosage form of about-1.0 µg/kg to 5.0 µg/kg.

8. The method of claim 1, wherein the dosage form comprises a total KLK1 polypeptide intravenous dosage form of about-0.5 µg/kg to about-3.0 µg/kg.

9. The method of claim 1, wherein the first KLK1 polypeptide and the second KLK1 polypeptides are present in the dosage form at a ratio of about 50:50.

10. The method of claim 1, wherein the first and second KLK1 polypeptides are recombinant KLK polypeptides, mature KLK1 polypeptides, human KLK1 (hKLK1) polypeptides, or any combination thereof.

11. The method of claim 10, wherein the hKLK1 polypeptides comprise, consist, or consist essentially of amino acid residues 78-141 of SEQ ID NO: 1 or amino acids residues 78-141 SEQ ID NO: 2, or an active fragment thereof, or an active variant having at least about 90, 95, 96, 97, 98, or 99% sequence identity to amino acid residues 78-141 of SEQ ID NO: 1 or amino acids residues 78-141 SEQ ID NO: 2.

12. The method of claim 10, wherein the hKLK1 polypeptides comprise, consist, or consist essentially of amino acid residues 25-262 of SEQ ID NO: 1 or amino acid residues 25-262 of SEQ ID NO: 2, or an active fragment thereof, or an active variant having at least about 90, 95, 96, 97, 98, or 99% sequence identity to amino acid residues 25-262 of SEQ ID NO: 1 or amino acid residues 25-262 of SEQ ID NO: 2.

13. The method of claim 10, wherein the hKLK1 polypeptides comprise an amino acid sequence having at least about 90, 95, 96, 97, 98, or 99% sequence identity to amino acid residues 25-262 of SEQ ID NO: 2, and wherein the hKLK1 polypeptides comprises E145 and/or A188.

14. The method of claim 10, wherein the hKLK1 polypeptides comprise an amino acid sequence having at least about 90, 95, 96, 97, 98, or 99% sequence identity to amino acid residues 25-262 of SEQ ID NO: 2, and wherein the hKLK1 polypeptides comprises Q145 and/or V188.

15. The method of claim 10, wherein the hKLK1 polypeptides comprise the amino acid sequence of SEQ ID NO: 4.

16. The method of claim 1, wherein the dosage form comprises a pharmaceutically acceptable excipient, diluent, adjuvant, or carrier.

17. The method of claim 1, wherein the dosage form is substantially free of other glycosylated isoforms (glycoforms) of KLK1.

18. The method of claim 1, wherein the dosage form has endotoxin levels of less than about 1 EU/mg protein, host cell protein of less than about 100 ng/mg total protein, host cell DNA of less than about 10 pg/mg total protein, and/or is substantially free of aggregates (as defined by being greater than about 95% appearing as a single peak by SEC HPLC).

* * * * *